(12) United States Patent
Glicklich

(10) Patent No.: US 11,426,377 B2
(45) Date of Patent: Aug. 30, 2022

(54) METHOD OF TREATING CONDITIONS RELATED TO THE PGI2 RECEPTOR

(71) Applicant: Arena Pharmaceuticals, Inc., San Diego, CA (US)

(72) Inventor: Alan Glicklich, San Diego, CA (US)

(73) Assignee: ARENA PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/227,740

(22) Filed: Apr. 12, 2021

(65) Prior Publication Data

US 2021/0290583 A1    Sep. 23, 2021

Related U.S. Application Data

(62) Division of application No. 16/870,777, filed on May 8, 2020, now Pat. No. 11,000,500, which is a division of application No. 16/706,424, filed on Dec. 6, 2019, now Pat. No. 10,688,076, which is a division of application No. 15/520,864, filed as application No. PCT/US2015/056824 on Oct. 22, 2015, now Pat. No. 10,537,546.

(60) Provisional application No. 62/067,916, filed on Oct. 23, 2014.

(51) Int. Cl.
| | | |
|---|---|---|
| *A61K 31/27* | (2006.01) | |
| *A61K 49/00* | (2006.01) | |
| *A61P 9/12* | (2006.01) | |
| *A61K 31/325* | (2006.01) | |
| *A61K 31/33* | (2006.01) | |
| *A61K 9/14* | (2006.01) | |
| *A61K 9/20* | (2006.01) | |
| *A61K 9/48* | (2006.01) | |

(52) U.S. Cl.
CPC .......... *A61K 31/325* (2013.01); *A61K 31/33* (2013.01); *A61P 9/12* (2018.01); *A61K 9/148* (2013.01); *A61K 9/20* (2013.01); *A61K 9/48* (2013.01)

(58) Field of Classification Search
CPC ...... A61K 31/325; A61K 31/33; A61K 9/148; A61K 9/20; A61K 9/48; A61K 31/27; A61K 49/0004; A61P 9/12
USPC ........................................................ 514/488
See application file for complete search history.

(56) References Cited

U.S. PATENT DOCUMENTS

| | | | |
|---|---|---|---|
| 5,849,919 A | 12/1998 | Hamanaka et al. | |
| 6,746,729 B1 | 6/2004 | Cherkaoui et al. | |
| 7,115,746 B2 | 10/2006 | Snoonian et al. | |
| 7,202,253 B2 | 4/2007 | Lloyd et al. | |
| 7,226,550 B2 | 6/2007 | Hou et al. | |
| 8,895,776 B2 | 11/2014 | Tran et al. | |
| 10,537,546 B2 | 1/2020 | Glicklich | |
| 10,688,076 B2 | 6/2020 | Glicklich | |
| 11,000,500 B2 | 5/2021 | Glicklich | |
| 2003/0144350 A1 | 7/2003 | Stevenson et al. | |
| 2004/0048844 A1 | 3/2004 | Nugiel et al. | |
| 2006/0063930 A1 | 3/2006 | Agoston et al. | |
| 2006/0258728 A1 | 11/2006 | Tani et al. | |
| 2011/0053958 A1 | 3/2011 | Tran et al. | |
| 2011/0224262 A1 | 9/2011 | Tran et al. | |
| 2011/0245251 A1 | 10/2011 | Tran et al. | |
| 2012/0225937 A1 | 9/2012 | Blackburn et al. | |
| 2013/0217706 A1 | 8/2013 | Tran et al. | |
| 2015/0126527 A1 | 5/2015 | Tran et al. | |

FOREIGN PATENT DOCUMENTS

| | | |
|---|---|---|
| CN | 1822808 A | 8/2006 |
| CN | 102036659 A | 4/2011 |
| EA | 200000012 A1 | 8/2000 |
| EP | 0028829 A1 | 5/1981 |
| EP | 0442448 A2 | 8/1991 |
| EP | 1046631 A1 | 10/2000 |
| EP | 1716087 A1 | 11/2006 |
| JP | H03160438 A | 7/1991 |
| JP | H06329598 A | 11/1994 |
| JP | H11269138 A | 10/1999 |
| JP | 2005104853 A | 4/2005 |
| JP | 2006083085 A | 3/2006 |
| JP | 2006137856 A | 6/2006 |
| JP | 2007161867 A | 6/2007 |
| JP | 2010539117 A | 12/2010 |
| JP | 2011515396 A | 5/2011 |
| WO | WO-02055484 A1 | 7/2002 |
| WO | WO-2007051255 A1 | 5/2007 |
| WO | WO-2007133653 A2 | 11/2007 |
| WO | WO-2009117095 A1 | 9/2009 |

(Continued)

OTHER PUBLICATIONS

Aguilar et al. Epoprostenol (prostacyclin) therapy in HIV-associated pulmonary hypertension. Am. J. Respir. Crit. Care Med. 162:1846-1850 (2000).

Archer et al., Nitric oxide deficiency in fenfluramine- and dexfenfluramine-induced pulmonary hypertension. Am. J. Respir. Crit. Care Med. 158:1061-1067 (1998).

Arehart et al., Acceleration of cardiovascular disease by a dysfunctional prostacyclin receptor mutation: potential implications for cyclooxygenase-2 inhibition. Circ. Res. 102(8):986-993 (2008).

(Continued)

*Primary Examiner* — Kristin A Vajda
(74) *Attorney, Agent, or Firm* — Wilson Sonsini Goodrich & Rosati

(57) ABSTRACT

Provided in some embodiments are titration packages, kits, and methods of treating pulmonary arterial hypertension comprising prescribing and/or administering to a patient in need thereof 2-(((1r,4r)-4-(((4-chlorophenyl)(phenyl)carbamoyloxy)methyl)cyclohexyl)methoxy)acetic acid (Compound 1), or a pharmaceutically acceptable salt, hydrate, or solvate thereof, via a titration scheme that comprises the up-titration of Compound 1, or a pharmaceutically acceptable salt, hydrate, or solvate thereof, over a period of no more than about nine weeks until an optimized dose is administered.

22 Claims, No Drawings

(56) References Cited

FOREIGN PATENT DOCUMENTS

| WO | WO-2010077275 A1 | 7/2010 |
|---|---|---|
| WO | WO-2011037613 A1 | 3/2011 |
| WO | WO-2016065103 A1 | 4/2016 |
| WO | WO-2018160882 A1 | 9/2018 |

OTHER PUBLICATIONS

Arehart et al., Prostacyclin, atherothrombosis, and cardiovascular disease. Curr. Med. Chem. 14:2161-2169 (2007).
Asada et al., Discovery of a series of acrylic acids and their derivatives as chemical leads for selective EP3 receptor antagonists, Bioorganic & Medicinal Chemistry, Pergamon, GB 17(18):6567-6582 (2009).
Badesch et al., Continuous intravenous epoprostenol for pulmonary hypertension due to the scleroderma spectrum of disease. A randomized, controlled trial. Ann. Intern. Med. 132:425-434 (2000).
Badesch et al., Prostanoid therapy for pulmonary arterial hypertension. Journal of the American College of Cardiology 43(12 Suppl. S):56S-61S (2004).
Baradia et al., Inhalation therapy to treat pulmonary arterial hypertension. Pharm. Pat. Analyst 1(5):577-588 (2012).
Berge et al. Pharmaceutical Salts. Journal of Pharmaceutical Sciences 66(1):1-19 (Jan. 1977).
Bernabei et al., Iloprost and echistatin protect platelets during simulated extracorporeal circulation. Ann. Thorac. Surg. 59:149-153 (1995).
BioWorld Today 22(133):1-7 URL: http://epozyme.com/pdf/bwt07132011.pdf (Jul. 13, 2011) (7 pgs).
Boehme et al., Decrease in circulating endothelial cell adhesion molecule and thrombomodulin levels during oral iloprost treatment in rheumatoid arthritis patients: preliminary results. Rheumatol. Int. 26:340-347 (2006).
Burnette et al. PGI2 opens potassium channels in retinal pericytes by cyclic AMP-stimulated, cross-activation of PKG. Exp. Eye Res. 83:1359-1365 (2006).
Cameron et al., The effects of 5-hydroxytryptamine 5-HT2 receptor antagonists on nerve conduction velocity and endoneurial perfusion in diabetic rats. Naunyn Schmiedebergs Arch. Pharmacol. 367:607-614 (2003).
Cameron. Vascular factors and metabolic interactions in the pathogenesis of diabetic neuropathy. Diabetologia 44:1973-1988 (2001).
Caojin et al., Comparison of acute hemodynamic effects of aerosolized iloprost and inhaled nitric oxide in adult congenital heart disease with severe pulmonary arterial hypertension. Department of Cardiology, Guangdong General Hospital & Guangdong Cardiovascular Institute, China, Intern Med. 51:2857-2862 (2012).
Chan. Vitamin E and atherosclerosis. J. Nutr. 128:1593-1596 (1998).
Cheng et al., Role of prostacyclin in the cardiovascular response to thromboxane A2. Science 296:539-541 (2002).
Chin et al. Long-term therapy with oral treprostinil in pulmonary arterial hypertension failed to lead to improvement in important physiologic measures: results from a single center. Pulm Circ 5(3):513-520 (2015).
Clinical Trials—Cancer. Genetic Engineering and Biotechnology News 32(20):54 (Nov. 15, 2012).
Collier et al., Radiosynthesis and in vivo evaluation of the pseudopeptide δ-opioid antagonist [125I]-ITIPP(ψ) J. Labelled Compd. Radiopharm 42:S264-S266 (1999).
Cote et al., Disruption of the nonneuronal tph1 gene demonstrates the importance of peripheral serotonin in cardiac function. PNAS 100(23):13525-13530 (2003).
Cotter et al., Prevention and reversal of motor and sensory peripheral nerve conduction abnormalities in streptozotocin-diabetic rats by the prostacyclin analogue iloprost. Naunyn Schmiedebergs Arch. Pharmacol. 347:534-540 (1993).
Czeslick et al., Inhibition of intracellular tumour necrosis factor (TNF)-alpha and interleukin (IL)-6 production in human monocytes by iloprost. Eur. J. Clin. Invest. 33:1013-1017 (2003).

Davi et al., Platelet activation and atherothrombosis. N. Eng. J. Med. 357:2482-2494 (2007).
Di Renzo et al., Iloprost treatment reduces TNF-alpha production and TNF-RII expression in critical limb ischemia patients without affecting IL6. Prostaglandin Leukot. Essent. Fatty Acids 73:405-410 (2005).
Dogan et al., Effect of the prostacyclin analogue, iloprost, on infarct size after permanent focal cerebral ischemia. Gen. Pharmacol. 27:1163-1166 (1996).
Driscoll et al., Medical therapy for pulmonary arterial hypertension. Expert Opin. Pharmacother. 9:65-81 (2008).
Drugs in Japan. Ethical Drugs 2008:2336-2337 (2009).
Egan et al., COX-2-derived prostacyclin confers atheroprotection on female mice. Science 306:1954-1957 (2004).
Fang et al., Induction of prostacyclin/PGI2 synthase expression after cerebral ischemia-reperfusion. J. Cereb. Blood Flow Metab. 26:491-501 (2006).
Fetalvero et al., Cardioprotective prostacyclin signaling in vascular smooth muscle. Prostaglandins Other Lipid Mediat. 82:109-118 (2007).
Fetalvero et al., The prostacyclin receptor induces human vascular smooth muscle cell differentiation via the protein kinase A pathway. Am. J. Physiol. Heart. Circ. Physiol. 290:H1337-H1346 (2006).
Fries et al., The cardiovascular pharmacology of COX-2 inhibition. Hematology Am. Soc. Hematol. Educ.Program, 2005:445-451 (2005).
Fujiwara et al., A stable prostacyclin analogue reduces high serum TNF-alpha levels in diabetic patients. Exp. Clin. Endocrinol. Diabetes 112:390-394 (2004).
Gabriel et al., High throughput screening technologies for direct cyclic AMP measurement. ASSAY and Drug Development Technologies, 1:291-303 (2003).
Gainza et al., Role of prostacyclin (epoprostenol) as anticoagulant in continuous renal replacement therapies: efficacy, security and cost analysis. J. Nephrol. 19:648-655 (2006).
Gao et al., A 7-day oral treatment of patients with active rheumatoid arthritis using the prostacyclin analog iloprost: cytokine modulation, safety, and clinical effects. Rheumatol. Int. 22:45-51 (2002).
Goya et al., Effects of the prostaglandin I2 analogue, beraprost sodium, on vascular cell adhesion molecule-1 expression in human vascular endothelial cells and circulating vascular cell adhesion molecule-1 level in patients with type 2 diabetes mellitus. Metabolism Clinical and Experimental 52:192-198 (2003).
Guillory. Chapters: Generation of Polymorphs, Hydrates, Solvates, and Amorphous Solids. Polymorphism in Pharmaceutical Solids pp. 183-226 (Brittain, H.G., ed., 1999).
Harada et al., Role of neutrophil elastase in development of pulmonary vascular injury and septic shock in rats. Shock 30(4):379-387 (2008).
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
Hoeper et al., Bosentan therapy for portopulmonary hypertension. Eur. Respir. J. 25:502-508 (2005).
Hoeper et al., Pulmonary hypertension after splenectomy? Ann. Intern. Med. 130(6):506-509 (1999).
Hotta et al., Effects of beraprost sodium and insulin on the electroretinogram, nerve conduction, and nerve blood flow in rats with streptozotocin-induced diabetes. Diabetes 45:361-366 (1996).
Hotta et al. Prevention of abnormalities in motor nerve conduction and nerve blood-flow by a prostacyclin analog, beraprost sodium, in streptozotocin-induced diabetic rats. Prostaglandins 49:339-349 (1995).
Hoyng et al., Iloprost, a stable prostacyclin analog, reduces intraocular pressure. Invest. Ophthalmol Vis. Sci. 28:470-476 (1987).
Humbert et al., Cellular and molecular pathobiology of pulmonary arterial hypertension. J. Am. Coll. Cardiol. 43:13S-24S (2004).
Humbert et al., Short-term and long-term epoprostenol (prostacyclin) therapy in pulmonary hypertension secondary to connective tissue diseases: results of a pilot study Eur. Respir. J. 13:1351-1356 (1999).
Idzko et al., Inhaled iloprost suppresses the cardinal features of asthma via inhibition of airway dendritic cell function. J. Clin. Invest. 117:464-472 (2007).

(56) References Cited

OTHER PUBLICATIONS

Indian Patent Application No. IN2006DN04486, 2006.
Indian Patent Application No. IN1995DE00358 358/DEL/1995, 1995.
Jaffar et al., Prostaglandin I2-IP signaling blocks allergic pulmonary inflammation by preventing recruitment of CD4+ Th2 cells into the airways in a mouse model of asthma. J. Immunol 179:6193-6203 (2007).
Jozefowski et al., Exogenous but not endogenous prostanoids regulate cytokine secretion from murine bone marrow dendritic cells: EP2, Dp, and IP but not EP1, EP3, and FP prostanoid receptors are involved. Int. Immunopharmcol. 3:865-878 (2003).
Klapars et al., A general and efficient copper catalyst for the amidation of aryl halides. J. Am. Chem. Soc. 124: 7421-7428 (2002).
Kobayashi et al., Roles of thromboxane A(2) and prostacyclin in the development of atherosclerosis in apoE-deficient mice. J. Clin. Invest. 114:784-794 (2004).
Koike et al., Enhanced angiogenesis and improvement of neuropathy by cotransfection of human hepatocyte growth factor and prostacyclin synthase gene. FASEB J. 17:779-781 (2003).
Le Bas et al., Radioiodinated analogs of EP 00652218 for the exploration of the tachykinin NK1 receptor by spect. J Labelled Compd. Radiopharm 44:S280-S282 (2001).
Liu et al., Treatments for pulmonary arterial hypertension. Respiratory Medicine, Baillier Tindall, London, GB 100(5):765-774 (2006).
Lundblad et al., Increased cortical cell loss and prolonged hemodynamic depression after traumatic brain injury in mice lacking the IP receptor for prostacyclin. Journal of Cerebral Blood Flow & Metabolism 28:367-376 (2008).
Mardla et al., Potentiation of antiaggregating effect of prostaglandins by alpha-tocopherol and quercetin. Platelets 15:319-324 (2004).
McCormick et al., Prostacyclin analogues: the next drug-eluting stent? Biochem. Soc. Trans. 35:910-911 (2007).
McGoon et al., Screening, early detection, and diagnosis of pulmonary arterial hypertension: ACCP evidence-based clinical practice guidelines. Chest 126:14S-34S (2004).
McLaughlin et al., Pulmonary arterial hypertension. Pulmonary arterial hypertension. Circulation 114(13):1417-1431 (2006).
Miwa et al., Combination therapy with oral sildenafil and beraprost for pulmonary arterial hypertension associated with CREST syndrome. Int. Heart J. 48:417-422 (2007).
Moncada et al., Human arterial and venous tissues generate prostacyclin (prostaglandin x), a potent inhibitor of platelet aggregation. Lancet 1:18-20 (1977).
Morecroft et al., Effect of tryptophan hydroxylase 1 deficiency on the development of hypoxia-induced pulmonary hypertension. Hypertension 49:232-236 (2007).
Moss. Basic terminology of stereochemistry (IUPAC Recommendations 1996). Pure & Appl. Chern. 68(12):2193-2222 (1996).
Muller et al., Iloprost has potent anti-inflammatory properties on human monocyte-derived dendritic cells. Clinical & Experimental Allergy, Department of Pneumology, University of Freiburg, Germany 40:1214-1221 (2010).
Murata et al., Altered pain perception and inflammatory response in mice lacking prostacyclin receptor. Nature 388:678-682 (1997).
Naeije et al., Expert opinion on available options treating pulmonary arterial hypertension. Expert Opin. Pharmacother. 8:2247-2265 (2007).
Nagao et al., Role of prostaglandin I2 in airway remodeling induced by repeated allergen challenge in mice. Am. J. Respir. Cell Mol. Biol. 29:314-320 (2003).
Okuda et al., Acute effect of beraprost sodium on lower limb circulation in patients with non-insulin-dependent diabetes mellitus-evaluation by color Doppler ultrasonography and laser cutaneous blood flowmetry. Prostaglandins 52:375-384 (1996).
Osol (Editor), Remington's Pharmaceutical Sciences, 1980, Philadelphia College of Pharmaceutical Science, Chapter 27: Structure-Activity Relationship and Drug Design, pp. 420-435.
Owada et al., Effect of long-term administration of prostaglandin I(2) in incipient diabetic nephropathy. Nephron 92:788-796 (2002).
PCT/US2015/056824 International Search Report and Written Opinion dated Jan. 12, 2016.
Potapov. Stereochemistry. 2nd Ed [Textbook for Chemistry Majors], USSR. (1988), p. 202, Publisher (Khimiya, Moscow, USSR) (English translation).
Rabinovitch. Pathobiology of pulmonary hypertension. Annu. Rev. Pathol. Meeh. Dis. 2:369-399 (2007).
Raychaudhuri et al., The prostacyclin analogue treprostinil blocks NFkappaB nuclear translocation in human alveolar macrophages. J. Biol. Chem. 277:33344-33348 (2002).
Robbins et al., Epoprostenol for treatment of pulmonary hypertension in patients with systemic lupus erythematosus. Chest 117:14-18 (2000).
Rosenkranz. Pulmonary hypertension: Current diagnosis and treatment. Clin. Res. Cardiol. 96(8):527-541 (2007).
Rosenzweig. Emerging treatments for pulmonary arterial hypertension. Expert Opin. Emerging Drugs 11 (4):609-619 (2006).
Rosenzweig et al., Long-term prostacyclin for pulmonary hypertension with associated congenital heart defects. Circulation 99:1858-1865 (1999).
Sato et al., Effect of OP-2507, a novel prostacyclin analogue on ischemia and reperfusion induced arrhythmias in isolated perfused rat heart. Journal of Molecular and Cellular Cardiology, Academic Press, GB, 22:S74 (1990).
Schermuly et al., Antiremodeling effects of iloprost and the dual-selective phosphodiesterase 3/4 inhibitor tolafentrine in chronic experimental pulmonary hypertension. Circ. Res. 94:1101-1108 (2004).
Seiler et al., 2-[3-[2-(4,5-Diphenyl-2-oxazolyl) ethyl] phenoxy] acetic acid (BMY 42393): a new, structurally-novel prostacyclin partial agonist: 1). Inhibition of platelet aggregation and mechanism of action. Thrombosis Research 74(2):115-123 (1994).
Semple. Discovery of APDS811: an orally available prostacylcin receptor agonist for the treatment of Pulmonary Arterial Hypertension (PAH). Presentation for 4th RSC/SCI GPCRS in Medicinal Chemistry, Sep. 17-19, 2012 Surrey UK (39 pgs).
Shindo et al., Clinical efficacy of a stable prostacyclin analog, iloprost, in diabetic neuropathy. Prostaglandins 41:85-96 (1991).
Shinomiya et al., Regulation of TNFalpha and interleukin-10 production by prostaglandins I(2) and E(2): studies with prostaglandin receptor-deficient mice and prostaglandin E-receptor subtype-selective synthetic agonists. Biochem. Pharmacol. 61:1153-1160 (2001).
Simonneau et al., Clinical classification of pulmonary hypertension. J. Am. Coll. Cardiol. 43:5S-12S (2004).
Stitham et al., Human prostacyclin receptor structure and function from naturally-occurring and synthetic mutations. Prostaglandins Other Lipid Mediat. 82:95-108 (2007).
Strauss et al., Prostanoid therapy for pulmonary arterial hypertension. Clin. Chest. Med. 28:127-142 (2007).
Streiter et al., The role of chelating diamine ligands in the goldberg reaction: a kinetic study on the copper-catalyzed amidation of aryl iodides. JACS Communications, J. Am. Chern. Soc. 127:4120-4121 (2005).
Szekeres et al., Delayed antiischemic effect of PgI2 and of a new stable PgI2 analogue 7-oxo-prostacyclin-Na in experimental model angina in dogs. Journal of Molecular and Cellular Cardiology, Academic Press, GB 15:132 (1983).
Taichman et al., Epidemiology of pulmonary arterial hypertension. Clin. Chest. Med., 28:1-22 (2007).
Takahashi et al., Augmentation of allergic inflammation in prostanoid IP receptor deficient mice. Br. J. Pharmacol, 137:315-322 (2002).
Tawara et al., Effects of combined therapy with a Rho-kinase inhibitor and prostacyclin on monocrotaline-induced pulmonary hypertension in rats. Journal of Cardiovascular Pharmacology 50(2):195-200 (2007).
Tennis et al., The role of prostacyclin in lung cancer. Translation Research, Division of Pulmonary Sciences and Critical Care Medicine, Department of Medicine, University of Colorado Denver Health Sciences, Denver, Colorado 155(2):57-61 (2010).

(56) References Cited

OTHER PUBLICATIONS

Tuder et al., Prostacyclin synthase expression is decreased in lungs from patients with severe pulmonary hypertension. Am. J. Respir. Crit. Care Med. 159:1925-1932 (1999).

Ueno et al., Effects of beraprost sodium, a prostacyclin analogue, on diabetic neuropathy in streptozotocin-induced diabetic rats. Jpn. J. Pharmacol, 70:177-182 (1996).

Ueno et al., Effects of beraprost sodium, a prostacyclin analogue, on tail flick response in two models of diabetic-neuropathy in rats and its mechanism. Life Sci. 59:PL105-PL110 (1996).

U.S. Appl. No. 16/870,777 Office Action dated Aug. 26, 2020.

Van Rijt et al., In vivo depletion of lung CD11c+ dendritic cells during allergen challenge abrogates the characteristic features of asthma. J. Exp. Med., 201:981-991 (2005).

Vippagunta et al., Crystalline solids. Advanced Drug Delivery Reviews 48:3-26 (2001).

Walther et al., Synthesis of serotonin by a second tryptophan hydroxylase isoform. Science 299:76 (2003).

Wang et al. Deletion of microsomal prostaglandin E synthase-1 augments prostacyclin and retards atherogenesis. Proc. Natl. Acad. Sci. USA 103:14507-14512 (2006).

Xiao et al., Roles of prostaglandin I(2) and thromboxane A(2) in cardiac ischemia-reperfusion injury: a study using mice lacking their respective receptors. Circulation 104:2210-2215 (2001).

Yamada et al., Hypotensive activity of novokinin, a potent analogue of ovokinin(2-7), is mediated by angiotensin AT(2) receptor and prostaglandin IP receptor. Peptides, 29:412-418 (2008).

Yamagishi et al., Beraprost sodium, a prostaglandin I2 analogue, protects against advanced gycation end products-induced injury in cultured retinal pericytes. Mol. Med. 8:546-550 (2002).

Yamashita et al., Beraprost sodium, prostacyclin analogue, attenuates glomerular hyperfiltration and glomerular macrophage infiltration by modulating ecNOS expression in diabetic rats. Diabetes Res. Clin. Pract. 57:149-161 (2002).

Zhang et al., Characterization of the molecular mechanisms of the coupling between intracellular loops of prostacyclin receptor with the C-terminal domain of the Galphas protein in human coronary artery smooth muscle cells. Arch. Biochem. Biophys. 454:80-88 (2006).

Zhou et al., Prostaglandin I2 analogs inhibit proinflammatory cytokine production and T cell stimulatory function of dendritic cells. J. Immunol. 178:702-710 (2007).

Zhu et al., Synthesis and mode of action of (125)I- and (3)H-labeled thieno[2,3-c]pyridine antagonists of cell adhesion molecule expression. J. Org. Chem. 67:943-948 (2002).

METHOD OF TREATING CONDITIONS RELATED TO THE PGI2 RECEPTOR

This application is a division of Ser. No. 16/870,777, filed May 8, 2020, which is a division of Ser. No. 16/706,424, filed Dec. 6, 2019, now U.S. Pat. No. 10,688,076, issued Jun. 23, 2020, which is a division of U.S. patent application Ser. No. 15/520,864, filed Apr. 21, 2017, now U.S. Pat. No. 10,537,546, issued Jan. 21, 2020, which is a U.S. National Stage entry of International Application No. PCT/US2015/056824, filed Oct. 22, 2015, which claims the benefit of priority from U.S. Provisional Patent Application No. 62/067,916, filed Oct. 23, 2014, all of which are hereby incorporated by reference in their entirety.

Provided are methods useful in the treatment of: pulmonary arterial hypertension (PAH); idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); and PAH with significant venous or capillary involvement.

Prostacyclin (PGI2) is a lipid molecule derived from arachidonic add through the cyclooxygenase pathway. It is a potent vasodilator, antiproliferative, anti-thrombotic and antiplatelet agent that mediates its effects as an agonist of a G protein-coupled receptor (PGI2 receptor; e.g., human PGI2 receptor, GenBank® Accession No. NP 000951 and alleles thereof). It is known that the binding of PGI2 (or other such agonist) to the PGI2 receptor leads to coupling with the Gs protein and increases intracellular cAMP levels. (See, e.g., Zhang et al, Arch. Biochem. Biophys., 2006, 454:80-88.)

Pulmonary arterial hypertension (PAH) is a life-threatening disease characterized by a progressive pulmonary vasculopathy leading to right ventricular hypertrophy. Right heart failure occurs if left untreated. Prostacyclin, which has vasodilatory and antiproliferative effects on the pulmonary vasculature has been found to be low in patients with PAH compared with normal controls. Exogenous administration of prostacyclin or an analog of prostacyclin {i.e., an agonist of the PGI2 receptor) has become an important strategy in the treatment of PAH. (See, e.g., Tuder et al, Am. J. Respir. Cut. Care. Med., 1999, 159: 1925-1932; Humbert et al, J. Am. Coll. Cardiol, 2004, 43:13S-24S; Rosenzweig, Expert Opin. Emerging Drugs, 2006, 11:609-619; McLaughlin et al, Circulation, 2006, 114:1417-1431; Rosenkranz, Clin. Res. Cardiol, 2007, 96:527-541; Driscoll et al, Expert Opin. Pharmacother., 2008, 9:65-81.)

Trepostinil and iloprost are FDA-approved analogs of prostacyclin which, like prostacyclin, are not orally-active. Beraprost is an orally-active analog of prostacyclin approved for the treatment of PAH in Japan, but it has failed registration for the treatment of PAH in Europe and in the US. Of the three FDA-approved drugs, prostacyclin is the best studied in PAH patients. The approximate annual cost of treating PAH with these drugs is $25,000 to $200,000 depending on the dose. At present, many experts consider intravenous prostacyclin to be the most reliable agent for managing the sickest PAH patients. Due to the short half-life of prostacyclin, intravenous treatment is complicated by the need for a continuous infusion. Patients are at risk for potentially fatal rebound pulmonary hypertension if the infusion is abruptly disrupted, as well as significant risk of catheter-related complications including sepsis. (See, e.g., Rosenzweig, Expert Opin. Emerging Drugs, 2006, 11:609-619; Naeije et ai, Expert Opin. Pharmacother., 2007, 8:2247-2265; Strauss et ai, Clin. Chest. Med., 2007, 28:127-142; Driscoll et ai, Expert Opin. Pharmacother., 2008, 9:65-81.)

2-(((1r,4r)-4-(((4-chlorophenyl)(phenyl)carbamoyloxy) methyl)cyclohexyl)methoxy (acetic acid (Compound 1), also known as APD811, an orally available agonist of the prostacyclin (IP) receptor, is disclosed in U.S. Patent Publication. No. 2011/0053958, incorporated by reference herein in its entirety. Compound 1 is an investigational drug candidate intended for the treatment of vasospastic diseases, such as Pulmonary Arterial Hypertension.

There exists a need for effectively treating patients who are in need of treatment with Compound 1. The present disclosure satisfies this need and provides related advantages as well.

SUMMARY

Provided is a method of treating pulmonary arterial hypertension comprising
  prescribing and/or administering to a patient in need thereof Compound 1, or a pharmaceutically acceptable salt, hydrate, or solvate thereof,
  wherein Compound 1, or a pharmaceutically acceptable salt, hydrate, or solvate thereof, is administered via a titration scheme that comprises the up-titration of Compound 1, or a pharmaceutically acceptable salt, hydrate, or solvate thereof, over a period of no more than about nine weeks until an optimized dose is administered.

Also provided is a method of determining an optimized dose for a patient in need of treatment of pulmonary arterial hypertension, comprising
  prescribing and/or administering to the patient Compound 1, or a pharmaceutically acceptable salt, hydrate, or solvate thereof, and
  increasing the dose of Compound 1, or a pharmaceutically acceptable salt, hydrate, or solvate thereof, over a period of no more than about nine weeks, until the optimized dose for the patient is administered.

Also provided is a method of determining an optimized dose for a patient in need of treatment with Compound 1, or a pharmaceutically acceptable salt, hydrate, or solvate thereof, comprising:
  prescribing and/or administering Compound 1, or a pharmaceutically acceptable salt, hydrate, or solvate thereof, to the patient at an initial dose equivalent to 0.01 mg of Compound 1 once daily for about one week; and
  determining whether the patient tolerates the initial dose;
wherein if the patient tolerates the initial dose, the dose is increased to a dose equivalent to 0.01 mg of Compound 1 twice daily;
wherein if the patient does not tolerate the initial dose, the optimized dose for the patient is less than a dose equivalent to 0.01 mg of Compound 1 once daily.

In some embodiments, the method of determining the optimized dose for the patient in need thereof further comprises:
  determining whether the patient tolerates the dose equivalent to 0.01 mg of Compound 1 twice daily;
  wherein if the patient tolerates the dose equivalent to 0.01 mg of Compound 1 twice daily, the dose is increased by an amount equal to a first incremental value;
  wherein if the patient does not tolerate the dose equivalent to 0.01 mg of Compound 1 twice daily, the optimized dose for the patient is a dose equivalent to 0.01 mg of Compound 1 once daily.

In some embodiments, the method of determining the optimized dose for the patient in need thereof further comprises:
prescribing and/or administering Compound 1, or a pharmaceutically acceptable salt, hydrate, or solvate thereof, to the patient at the increased dose for about one week; and
determining whether the patient tolerates the increased dose;
wherein if the patient tolerates the increased dose, the dose is further increased by an amount equal to a second incremental value, wherein the second incremental value is the same or different from the first incremental value;
wherein if the patient does not tolerate the increased dose, the optimized dose for the patient is equal to the difference between the increased dose and the first incremental value.

Also provided is a method of determining an optimized dose for a patient in need of treatment with Compound 1, or a pharmaceutically acceptable salt, hydrate, or solvate thereof, comprising:
prescribing and/or administering Compound 1, or a pharmaceutically acceptable salt, hydrate, or solvate thereof, to the patient at an initial dose equivalent to 0.01 mg of Compound 1 twice daily for about one week;
determining whether the patient tolerates the initial dose; and
wherein if the patient tolerates the initial dose, the dose is increased by an amount equal to a first incremental value;
wherein if the patient does not tolerate the initial dose, the optimized dose for the patient is less than a dose equivalent to 0.01 mg of Compound 1 twice daily.

In some embodiments, the method of determining the optimized dose for the patient in need thereof further comprises:
prescribing and/or administering Compound 1, or a pharmaceutically acceptable salt, hydrate, or solvate thereof, to the patient at the increased dose for about one week; and
determining whether the patient tolerates the increased dose;
wherein if the patient tolerates the increased dose, the dose is further increased by an amount equal to a second incremental value, wherein the second incremental value is the same or different from the first incremental value;
wherein if the patient does not tolerate the increased dose, the optimized dose for the patient is equal to the difference between the increased dose and the first incremental value.

Also provided is a method of determining an optimized dose for a patient in need of treatment with Compound 1, or a pharmaceutically acceptable salt, hydrate, or solvate thereof, comprising a cycle of:
prescribing and/or administering to the patient the increased dose for a period of about one week;
further increasing the dose by an amount equal to an incremental value; and
determining whether the patient tolerates the further increased dose;
wherein the cycle is repeated so long as the patient tolerates the further increased dose, wherein the incremental value at each cycle repetition is the same or different; and
wherein if the patient does not tolerate the further increased dose, the optimized dose for the patient is equal to the difference between the further increased dose and the incremental value for the last cycle repetition.

Also provided is a titration package for enabling compliance with a regimen of changing dosage of medication over a period of time, wherein the medication is Compound 1, or a pharmaceutically acceptable salt, hydrate, or solvate thereof, the package comprising:
a backing having an array of receivers, said array including a plurality of columns and a plurality of rows;
a plurality of sets of solid dosage forms, each solid dosage form in a set having a common dose of the medication and a different dose than a solid dosage form of a different set, each set being disposed in receivers of one of an adjacent row and an adjacent column; different sets of solid dosage forms are disposed in different rows, each row being indicated as a successive time period, each column being indicated as a different day of the time period, sets of solid dosage forms having increased doses being disposed in receivers of rows indicated as successive time periods; and indicia disposed adjacent the columns and rows for displaying common days and successive time periods.

Also provided is a kit comprising a titration package as disclosed herein and instructions indicating that the medication is to be administered to a patient in need of treatment of pulmonary arterial hypertension.

Also provided is a method of treating pulmonary arterial hypertension comprising providing a titration package as disclosed herein to patient in need thereof.

Also provided is a method of determining an optimized dose for a patient in need of treatment of pulmonary arterial hypertension, comprising
prescribing and/or administering to the patient Compound 1, or a pharmaceutically acceptable salt, hydrate, or solvate thereof, and
increasing the dose of Compound 1, or a pharmaceutically acceptable salt, hydrate, or solvate thereof, over a period of no more than about nine weeks.

DETAILED DESCRIPTION

As used in the present specification, the following words and phrases are generally intended to have the meanings as set forth below, except to the extent that the context in which they are used indicates otherwise.

COMPOUND 1: As used herein, "Compound 1" refers to 2-(((1r,4r)-4-(((4-ehlorophenyiXphenyl)carbamoyloxy) methyl)eyclohexyl)methoxy)aeetic acid including crystalline forms thereof. As a non-limiting example, Compound 1 may be present in the crystalline form disclosed in WO2009117095 (incorporated by reference herein in its entirety), which may be characterized by one or more of the following °2Θ values for the peaks in the PXRD spectrum: 8.9, 10.8, 11.9, 15.2, 16.4, 16.8, 18.9, 20.3, 207 and 21.5, wherein the reported peaks can vary by about ±0.2°2Θ.

ADMINISTERING: As used herein, "administering" means to provide a compound or other therapy, remedy or treatment. For example, a health care practitioner can directly provide a compound to a patient in the form of a sample, or can indirectly provide a compound to a patient by providing an oral or written prescription for the compound. Also, for example, a patient can obtain a compound by themselves without the involvement of a health care practitioner. Administration of the compound may or m ay not involve the patient actually internalizing the compound. In the case where a patient internalizes the compound the body is transformed by the compound in some way.

PRESCRIBING: As used herein, "prescribing" means to order, authorize or recommend the use of a drug or other therapy, remedy or treatment. In some embodiments, a health care practitioner can orally advise, recommend or authorize the use of a compound, dosage regimen or other treatment to a patient. In this case the health care practitioner may or may not provide a prescription for the compound, dosage regimen or treatment. Further, the health care practitioner may or may not provide the recommended compound or treatment. For example, the health care practitioner can advise the patient where to obtain the compound without providing the compound. In some embodiments, a health care practitioner can provide a prescription for the compound, dosage regimen or treatment to the patient. For example, a health care practitioner can give a written or oral prescription to a patient, A prescription can be written on paper or on electronic media such as a computer file, for example, on a hand held computer device. For example, a health care practitioner can transform a piece of paper or electronic media with a prescription for a compound, dosage regimen or treatment. In addition, a prescription can be called in (oral) or faxed in (written) to a pharmacy or a dispensary. In some embodiments, a sample of the compound or treatment can be given to the patient. As used herein, giving a sample of a compound constitutes an implicit prescription for the compound. Different health care systems around the world use different methods for prescribing and/or administering compounds or treatments and these methods are encompassed by the disclosure.

A prescription can include, for example, a patient's name and/or identifying information such as date of birth. In addition, for example, a prescription can include, the medication name, medication strength, dose, frequency of administration, route of administration, number or amount to be dispensed, number of refills, physician name, physician signature. Further, for example, a prescription can include a DEA number or state number.

A healthcare practitioner can include, for example, a physician, nurse, nurse practitioner or other related health care professional who can prescribe or administer compounds (drugs) for weight management. In addition, a healthcare practitioner can include anyone who can recommend, prescribe, administer or prevent a patient from receiving a compound or drug, including, for example, an insurance provider.

PREVENT, PREVENTING, OR PREVENTION: As used herein, the term "prevent," "preventing" or "prevention" such as prevention of obesity means prevention of the occurrence or onset of one or more symptoms associated with a particular disorder and does not necessarily mean the complete prevention of a disorder. For example, the term "prevent," "preventing" and "prevention" refers to the administration of therapy on a prophylactic or preventative basis to a patient who may ultimately manifest at least one symptom of a disease or condition but who has not yet done so. Such patients can be identified on the basis of risk factors that are known to correlate with the subsequent occurrence of the disease. Alternatively, prevention therapy can be administered without prior identification of a risk factor, as a prophylactic measure. Delaying the onset of toe at least one symptom can also be considered prevention or prophylaxis.

TREAT, TREATING, OR TREATMENT: As used herein the term "treat," "treating" or "treatment" refers to the administration of therapy to a patient who already manifests at least one symptom of a disease or condition or who has previously manifested at least one symptom of a disease or condition. For example, "treating" can include alleviating, abating or ameliorating a disease or condition symptoms, preventing additional symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder.

TOLERATE: As used herein, a patient is said to "tolerate" a dose of a compound if administration of that dose to that patient does not result in an unacceptable adverse event or an unacceptable combination of adverse events. One of skill in the art will appreciate that tolerance is a subjective measure and that what may be tolerable to one patient may not be tolerable to a different patient. For example, one patient may not be able to tolerate headache, whereas a second patient may find headache tolerable but is not able to tolerate vomiting, whereas for a third patient, either headache alone or vomiting alone is tolerable, but the patient is not able to tolerate the combination of headache and vomiting, even if the severity of each is less than when experienced alone.

ADVERSE EVENT: As used herein, an "adverse event" is an untoward medical occurrence that is associated with treatment with Compound 1 or a pharmaceutically acceptable salt, solvate or hydrate thereof. In one embodiment, an adverse event is selected from headache, nausea, vomiting, and jaw pain. In one embodiment, an adverse event is selected from headache, nausea, vomiting, jaw pain, flushing, abnormal pulse rate, abnormal QT interval, sitting systolic blood pressure >160 mmHg, sitting diastolic blood pressure >100 mmHg, systolic blood pressure <90 mmHg, or a combination of one more of the foregoing. In one embodiment, an adverse event is selected from abdominal pain, nosebleed, muscle aches, feeling of warmth, palpitations, dizziness, itching, diarrhea, chest pressure, joint aches, prickling or tingling skin sensation, and lowering of blood pressure. In one embodiment, an adverse event is selected from chest pain, chest discomfort, and erythema.

OPTIMIZED DOSE: As used herein, an "optimized dose" refers a therapeutic dose optimized to the needs of a specific patient and is the highest dose of Compound 1, or the dose of a pharmaceutically acceptable salt, solvate, or hydrate thereof that is equivalent to the highest dose of Compound 1, that elicits the biological or medicinal response in the patient that is being sought and that can be tolerated by the patient, as determined by the patient, optionally in consultation with the patient's healthcare practitioner. The amount of Compound 1 in an optimized dose may vary between patients. Further, the amount of Compound 1 may vary from time to time for a given patient.

UP-TITRATION: As used herein, "up-titration" of a compound refers to increasing the amount of a compound until the patient does not tolerate the increased amount. Up-titration can be achieved in one or more dose increments, which may be the same or different. In some embodiments, the method comprises prescribing and/or administering Compound 1 or a pharmaceutically acceptable salt, solvate or hydrate thereof in an amount equivalent to 0.01 mg of Compound 1 2 times daily for about one week, followed by up-titration as disclosed herein until an optimized dose is administered. Administration of the optimized dose twice daily may then continue as long as necessary. in some embodiments, the method comprises prescribing and/or administering Compound 1 or a pharmaceutically acceptable salt, solvate or hydrate thereof in an amount equivalent to 0.01 mg of Compound 1 once daily for about one week, followed by up-titration to an amount equivalent to 0.01 mg of Compound 1 twice daily for about one week, followed by up-titration as disclosed herein until an optimized dose is administered. Administration of the optimized dose twice daily may then continue as long as necessary.

It is understood that when the phrase "pharmaceutically acceptable salts, solvates and hydrates" or the phrase "pharmaceutically acceptable salt, solvate or hydrate" is used when referring to Compound 1, it embraces pharmaceutically acceptable solvates and/or hydrates of Compound 1, pharmaceutically acceptable salts of Compound 1, as well as pharmaceutically acceptable solvates and/or hydrates of pharmaceutically acceptable salts of Compound 1. It is also understood that when the phrase "pharmaceutically acceptable solvates and hydrates" or the phrase "pharmaceutically acceptable solvate or hydrate" is used when referring to Compound 1 that are salts, it embraces pharmaceutically acceptable solvates and/or hydrates of such salts.

It will be apparent to those skilled in the art that the dosage forms described herein may comprise, as the active component, either Compound 1 or a pharmaceutically acceptable salt or as a solvate or hydrate thereof. Moreover, various hydrates and solvates of Compound 1 and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present disclosure pertains to methods of prescribing and/or administering hydrates and solvates of Compound 1 and/or its pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The present disclosure includes all isotopes of atoms occurring in the present compounds, salts, solvates, and hydrates. Isotopes include those atoms having the same atomic number but different mass numbers. One aspect of the present invention includes every combination of one or more atoms in the present compounds, salts, solvates, and hydrates that is replaced with an atom having the same atomic number but a different mass number. One such example is the replacement of an atom that is the most naturally abundant isotope, such as $^1$H or $^{12}$C, found in one the present compounds, salts, solvates, and hydrates, with a different atom that is not the most naturally abundant isotope, such as $^2$H or $^3$H (replacing $^1$H), or $^{11}$C, $^{13}$C, or $^{14}$C (replacing $^{12}$C). A salt wherein such a replacement has taken place is commonly referred to as being isotopically-labeled. Isotopic-labeling of the present compounds, salts, solvates, and hydrates can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$C. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{135}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, salts, solvates, and hydrates, wherein the naturally occurring distribution of the isotopes in the composition is perturbed. Another aspect of the present invention includes compositions and pharmaceutical compositions comprising the compounds, salts, solvates, and hydrates, as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

As used herein, the term "greater than" is used interchangeably with the symbol > and the term less than is used interchangeably with the symbol <. Likewise the term less than or equal to is interchangeably with the symbol ≤.

When an integer is used in a method disclosed herein, the term "about" can be inserted before the integer.

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination. For example, a method that recites prescribing and/or administering Compound 1 or a pharmaceutically acceptable salt, solvate or hydrate thereof can be separated into two methods; one reciting prescribing Compound 1 or a pharmaceutically acceptable salt, solvate or hydrate thereof and the other reciting administering Compound 1 or a pharmaceutically acceptable salt, solvate or hydrate thereof. In addition, for example, a method that recites prescribing Compound 1 or a pharmaceutically acceptable salt, solvate or hydrate thereof and a separate method of the invention reciting administering Compound 1 or a pharmaceutically acceptable salt, solvate or hydrate thereof can be combined into a single method reciting prescribing and/or administering Compound 1 or a pharmaceutically acceptable salt, solvate or hydrate thereof.

Provided is a method of treating pulmonary arterial hypertension comprising
  prescribing and/or administering to a patient in need thereof Compound 1, or a pharmaceutically acceptable salt, hydrate, or solvate thereof,
  wherein the Compound 1, or a pharmaceutically acceptable salt, hydrate, or solvate thereof, is administered via a titration scheme that comprises the up-titration of Compound 1, or a pharmaceutically acceptable salt, hydrate, or solvate thereof, over a period of no more than about nine weeks until an optimized dose is administered.

Also provided is a method of determining an optimized dose for a patient in need of treatment of pulmonary arterial hypertension, comprising
  prescribing and/or administering to the patient Compound 1, or a pharmaceutically acceptable salt, hydrate, or solvate thereof, and
  increasing the dose of Compound 1, or a pharmaceutically acceptable salt, hydrate, or solvate thereof, over a period of no more than about nine weeks, until the optimized dose for the patient is administered.

Also provided is a method of determining an optimized dose for a patient in need of treatment with Compound 1, or a pharmaceutically acceptable salt, hydrate, or solvate thereof, comprising:
  prescribing and/or administering Compound 1, or a pharmaceutically acceptable salt, hydrate, or solvate thereof, to the patient at an initial dose equivalent to 0.01 mg of Compound 1 once daily for about one week; and
  determining whether the patient tolerates the initial dose;
  wherein if the patient tolerates the initial dose, the dose is increased to a dose equivalent to 0.01 mg of Compound 1 twice daily;
  wherein if the patient does not tolerate the initial dose, the optimized dose for the patient is less than a dose equivalent to 0.01 mg of Compound 1 once daily.

In some embodiments, the method of determining the optimized dose for the patient in need thereof further comprises:
  determining whether the patient tolerates the dose equivalent to 0.01 mg of Compound 1 twice daily;
  wherein if the patient tolerates the dose equivalent to 0.01 mg of Compound 1 twice daily, the dose is increased by an amount equal to a first incremental value;
  wherein if the patient does not tolerate the dose equivalent to 0.01 mg of Compound 1 twice daily, the optimized dose for the patient is less than a dose equivalent to 0.01 mg of Compound 1 twice daily.

In some embodiments, the method of determining the optimized dose for the patient in need thereof further comprises:
  prescribing and/or administering Compound 1, or a pharmaceutically acceptable salt, hydrate, or solvate thereof, to the patient at the increased dose for about one week; and
  determining whether the patient tolerates the increased dose;
  wherein if the patient tolerates the increased dose, the dose is further increased by an amount equal to a second incremental value, wherein the second incremental value is the same or different from the first incremental value;
  wherein if the patient does not tolerate the increased dose, the optimized dose for the patient is equal to the difference between the increased dose and the first incremental value.

Also provided is a method of determining an optimized dose for a patient in need thereof comprises:
  prescribing and/or administering Compound 1, or a pharmaceutically acceptable salt, hydrate, or solvate thereof, at an initial dose equivalent to 0.01 mg of Compound 1 twice daily for about one week; and
  determining whether the patient tolerates the initial dose;
  wherein if the patient tolerates the initial dose, the dose is increased by an amount equal to a first incremental value; and
  wherein if the patient does not tolerate the initial dose, the optimized dose for the patient is less than the equivalent of 0.01 mg of Compound 1 twice daily.

In some embodiments, the method of determining an optimized dose for the patient further comprises:
  prescribing and/or administering Compound 1, or a pharmaceutically acceptable salt, hydrate, or solvate thereof, at the increased dose for about one week; and
  determining whether the patient tolerates the increased dose;
  wherein if the patient tolerates the increased dose, the dose is further increased by an amount equal to a second incremental value, wherein the second incremental value is the same or different from the first incremental value;
  wherein if the patient does not tolerate the increased dose, the optimized dose for the patient is equal to the difference between the increased dose and the first incremental value.

Also provided is a method of determining an optimized dose for a patient in need thereof comprising a cycle of:
  prescribing and/or administering the increased dose for a period of about one week;
  further increasing the dose by an amount equal to an incremental value; and
  determining whether the patient tolerates the further increased dose;

wherein the cycle is repeated so long as the patient tolerates the further increased dose, wherein the incremental value at each cycle repetition is the same or different; and wherein if the patient does not tolerate the further increased dose, the optimized dose for the patient is equal to the difference between the further increased dose and the incremental value for the last cycle repetition.

In some embodiments the method further comprises prescribing and/or administering the optimized dose of Compound 1, or a pharmaceutically acceptable salt, hydrate, or solvate thereof, to the patient.

In some embodiments the up-titration is performed over a period of about 9 weeks.

In some embodiments the amount of Compound 1, or a pharmaceutically acceptable salt, hydrate, or solvate thereof, administered to the patient is increased at intervals of about equal time periods until the optimized dose is administered. In some embodiments, the amount is increased at about weekly intervals.

In some embodiments, the titration scheme comprises prescribing and/or administering Compound 1, or a pharmaceutically acceptable salt, hydrate, or solvate thereof, at an initial dose equivalent to 0.01 mg of Compound 1 twice daily for about one week and, provided that the patient tolerates the initial dose, increasing the dose.

In some embodiments, the titration scheme further comprises prescribing and/or administering Compound 1, or a pharmaceutically acceptable salt, hydrate, or solvate thereof, at the increased dose for about one week and, provided that the patient tolerates the increased dose, further increasing the dose.

In some embodiments, the titration scheme comprises a cycle of prescribing and/or administering the increased dose for a period of about one week and then further increasing the dose, wherein the cycle is repeated so long as the patient tolerates the further increased dose, until an optimized dose is administered.

In some embodiments where the titration scheme comprises a cycle of prescribing and/or administering the increased dose as disclosed herein, the cycle is repeated once. In some embodiments, the cycle is repeated twice. In some embodiments, the cycle is repeated three times. In some embodiments, the cycle is repeated four times. In some embodiments, the cycle is five times. In some embodiments, the cycle is repeated six times. In some embodiments, the cycle is repeated seven times. In some embodiments, the cycle is repeated eight times. In some embodiments, the cycle is repeated nine times. In some embodiments, the cycle is not repeated.

In some embodiments of the method of treating pulmonary arterial hypertension comprising administration via a titration scheme, the titration scheme comprises a cycle of
1) prescribing and/or administering for a period of about one week a dose that is higher by an incremental value than the dose for a previous period, and
2) determining whether the patient tolerates the higher dose for such period of about one week;
   wherein the cycle of steps 1) and 2) is repeated so long as the patient tolerates the higher dose, wherein the incremental value at every repetition of the cycle is the same or different from a previous incremental value;
   wherein if the patient does not tolerate the higher dose, the optimized dose for the patient is equal to the difference between the higher dose and the incremental value for the last cycle repetition.

In some embodiments of the method of determining the optimized dose for the patient in need thereof, the method comprises prescribing and/or administering Compound 1, or a pharmaceutically acceptable salt, hydrate, or solvate thereof, over more than one period each of about one week, wherein the method comprises a cycle of
1) prescribing and/or administering for a period of about one week a dose that is higher by an incremental value than the dose for a previous period, and
2) determining whether the patient tolerates the higher dose for such period of about one week;
   wherein the cycle of steps 1) and 2) is repeated so long as the patient tolerates the higher dose, wherein the incremental value at every repetition of the cycle is the same or different from a previous incremental value;
   wherein if the patient does not tolerate the higher dose, the optimized dose for the patient is equal to the difference between the higher dose and the incremental value for the last cycle repetition.

In some embodiments of the cycle of
1) prescribing and/or administering for a period of about one week a dose that is higher by an incremental value than the dose for a previous period, and
2) determining whether the patient tolerates the higher dose for such period of about one week,
   the higher dose administered is equal to an amount administered twice daily that is higher than the amount administered twice daily for a previous period is, and determining whether the patient tolerates the higher dose comprises:
   a) determining whether the patient tolerates the higher amount administered twice daily;
   b) if the patient does not tolerate the higher amount administered twice daily, administering the higher amount once daily to the patient;
   c) if the patient tolerates the higher amount administered once daily, re-administering the higher amount twice daily to the patient; and
   d) determining if the patient tolerates the higher amount re-administered twice daily.

In some embodiments, determining whether the patient tolerates the higher dose comprises:
   a) determining whether the patient tolerates the higher amount administered twice daily;
   b) if the patient does not tolerate the higher amount administered twice daily, administering the higher amount once daily to the patient;
   c) if the patient tolerates the higher amount administered once daily, re-administering the higher amount twice daily to the patient; and
   d) determining if the patient tolerates the higher amount re-administered twice daily.

In some embodiments, the patient does not tolerate the initial dose and the optimized dose of Compound 1, or a pharmaceutically acceptable salt, hydrate, or solvate thereof, is less than the equivalent of 0.01 mg of Compound 1 once daily. In some embodiments, the optimized dose of Compound 1, or a pharmaceutically acceptable salt, hydrate, or solvate thereof, is the equivalent of 0.01 mg of Compound 1 administered at a frequency that is less than twice daily.

In some embodiments, the optimized dose of Compound 1, or a pharmaceutically acceptable salt, hydrate, or solvate thereof, is equivalent to 0.01 mg of Compound 1 once daily.

In some embodiments, the optimized dose of Compound 1, or a pharmaceutically acceptable salt, hydrate, or solvate thereof, is equivalent to 0.01 mg of Compound 1 twice daily.

In some embodiments, the optimized dose of Compound 1, or a pharmaceutically acceptable salt, hydrate, or solvate thereof, is equivalent to 0.02 mg of Compound 1 twice daily.

In some embodiments, the optimized dose of Compound 1, or a pharmaceutically acceptable salt, hydrate, or solvate thereof, is equivalent to 0.03 mg of Compound 1 twice daily.

In some embodiments, the optimized dose of Compound 1, or a pharmaceutically acceptable salt, hydrate, or solvate thereof, is equivalent to 0.04 mg of Compound 1 twice daily.

In some embodiments, the optimized dose of Compound 1, or a pharmaceutically acceptable salt, hydrate, or solvate thereof, is equivalent to 0.06 mg of Compound 1 twice daily.

In some embodiments, the optimized dose of Compound 1, or a pharmaceutically acceptable salt, hydrate, or solvate thereof, is equivalent to 0.08 mg of Compound 1 twice daily.

In some embodiments, the optimized dose of Compound 1, or a pharmaceutically acceptable salt, hydrate, or solvate thereof, is equivalent to 0.1 mg of Compound 1 twice daily.

In some embodiments, the optimized dose of Compound 1, or a pharmaceutically acceptable salt, hydrate, or solvate thereof, is equivalent to 0.2 mg of Compound 1 twice daily.

In some embodiments, the optimized dose of Compound 1, or a pharmaceutically acceptable salt, hydrate, or solvate thereof, is equivalent to 0.3 mg of Compound 1 twice daily.

In some embodiments, the optimized dose of Compound 1, or a pharmaceutically acceptable salt, hydrate, or solvate thereof, is equivalent to 0.6 mg of Compound 1 twice daily.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration. In some embodiments, the Compound 1, or a pharmaceutically acceptable salt, hydrate, or solvate thereof, is formulated as a capsule.

In some embodiments, the Compound 1, or a pharmaceutically acceptable salt, hydrate, or solvate thereof, is Compound 1, or a hydrate or solvate thereof.

In some embodiments, the Compound 1, or a pharmaceutically acceptable salt, hydrate, or solvate thereof, is Compound 1.

In some embodiments, provided here is a pharmaceutical composition comprising an amount of Compound 1, or a pharmaceutically acceptable salt, hydrate, or solvate thereof, equivalent to 0.01 mg of Compound 1.

In some embodiments, provided here is a pharmaceutical composition comprising an amount of Compound 1, or a pharmaceutically acceptable salt, hydrate, or solvate thereof, equivalent to 0.02 mg of Compound 1.

In some embodiments, provided here is a pharmaceutical composition comprising an amount of Compound 1, or a pharmaceutically acceptable salt, hydrate, or solvate thereof, equivalent to 0.03 mg of Compound 1.

In some embodiments, provided here is a pharmaceutical composition comprising an amount of Compound 1, or a pharmaceutically acceptable salt, hydrate, or solvate thereof, equivalent to 0.04 mg of Compound 1.

In some embodiments, provided here is a pharmaceutical composition comprising an amount of Compound 1, or a pharmaceutically acceptable salt, hydrate, or solvate thereof, equivalent to 0.06 mg of Compound 1.

In some embodiments, provided here is a pharmaceutical composition comprising an amount of Compound 1, or a pharmaceutically acceptable salt, hydrate, or solvate thereof, equivalent to 0.08 mg of Compound 1.

In some embodiments, provided here is a pharmaceutical composition comprising an amount of Compound 1, or a pharmaceutically acceptable salt, hydrate, or solvate thereof, equivalent to 0.1 mg of Compound 1.

In some embodiments, provided here is a pharmaceutical composition comprising an amount of Compound 1, or a pharmaceutically acceptable salt, hydrate, or solvate thereof, equivalent to 0.2 mg of Compound 1.

In some embodiments, provided here is a pharmaceutical composition comprising an amount of Compound 1, or a pharmaceutically acceptable salt, hydrate, or solvate thereof, equivalent to 0.3 mg of Compound 1.

In some embodiments, provided here is a pharmaceutical composition comprising an amount of Compound 1, or a pharmaceutically acceptable salt, hydrate, or solvate thereof, equivalent to 0.6 mg of Compound 1.

In some embodiments, provided here is a pharmaceutical composition comprising an amount of Compound 1, or a pharmaceutically acceptable salt, hydrate, or solvate thereof, equivalent to 0.01 mg to 0.6 mg of Compound 1, such as 0.01 mg to 0.3 mg of Compound 1, such as 0.01 mg to 0.2 mg of Compound 1, such as 0.01 mg to 0.1 mg of Compound 1, such as 0.02 mg to 0.08 mg of Compound 1, such as 0.03 mg to 0.06 mg of Compound 1, such as such as 0.04 mg of Compound 1.

In some embodiments of the pharmaceutical composition, the composition is in the form of a capsule or tablet. In some embodiments of the pharmaceutical composition, the composition is in the form of a capsule. In some embodiments of the pharmaceutical composition, the composition is in the form of a tablet.

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al. J. Am. Coll. Cardiol, 2004, 43:13 S-24S.)

The compounds disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (IPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HIV infection, PAH associated with drugs or toxins, or PAH associated with Other; and PAH associated with significant venous or capillary involvement.

Idiopathic PAH refers to PAH of undetermined cause.

Familial PAH refers to PAH for which hereditary transmission is suspected or documented.

PAH associated with collagen vascular disease shall be understood to encompass PAH associated with scleroderma, PAH associated with CREST (calcinosis cutis, Raynaud's phenomenon, esophageal dysfunction, sclerodactyl), and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis.

PAH associated with congenital systemic-to-pulmonary shunts shad be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of aminorex, PAH associated with ingestion of a fenfluramine compound (e.g., PAH associated with ingestion of fenfluramine or PAH associated with ingestion of dexfenfluramine), PAH associated with ingestion of certain toxic oils (e.g., PAH associated with ingestion of rapeseed oil), PAH associated with ingestion of pyrrolizidine alkaloids (e.g., PAH associated with ingestion of bush tea) and PAH associated with ingestion of monocrotaline.

PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy.

PAH associated with significant venous or capillary involvement shall be understood to encompass PAH associated with pulmonary veno-occlusive disease (PVOD) and PAH associated with pulmonary capillary hemangiomatosis (PCH). (See, e.g., Simonneau et al. J. Am. Coll. Cardiol, 2004, 43:5 S-12S; McGoon et al. Chest, 2004, 126:14 S-34S; Rabinovitch, Annu, Rev. Pathol. Mech. Dis., 2007, 2:369-399; McLaughlin et al. Circulation, 2006, 114:1417-1431; Strauss et al. Clin, Chest. Med., 2007, 28:127-142; Taichman et al. Clin. Chest. Med., 2007, 28:1-22.)

Evidence for the association of PAH with scleroderma and the beneficial effect of an agonist of the PGI2 receptor on PAH is given by Badesch et ah (Badesch et al. Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the PGI2 receptor on PAH is given by Humbert et al. (Eur. Respir. J., 1999, 13:1351-1356). Evidence for the association of PAH with CREST syndrome and the beneficial effect of an agonist of the PGI2 receptor on PAH is given by Miwa et al. (Int. Heart J., 2007, 48:417422). Evidence for the association of PAH with SEE and the beneficial effect of an agonist of the PGI2 receptor on PAH is given by Robbins et al. (Chest, 2000, 117:14-1.8). Evidence for the association of PAH with HIV infection and the beneficial effect of an agonist of the PGI2 receptor on PAH is given by Aguilar et al. (Am. J. Respir, Crit. Care Med., 2000, 162:1846-1850). Evidence for the association of PAH with congenital heart defects (including ASD, VSD and patent ductus arteriosus) and the beneficial effect of an agonist of the PGI2 receptor on PAH is given by Rosenzweig et al. (Circulation, 1999, 99:1858-1865). Evidence for the association of PAH with fenfluramine and with dexfenfluramine, anorexigens, is given by Archer et al. (Am. J. Respir. Crit. Care Med., 1998, 158:1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the PGI2 receptor on PAH is given by Hoeper et al. (Eur. Respir. J., 2005, 25:502-508).

Symptoms of PAH include dyspnea, angina, syncope and edema (McLaughlin et al. Circulation, 2006.114:1417-1431). The compounds disclosed herein are useful in the treatment of symptoms of PAH.

In some embodiments, pulmonary arterial hypertension (PAH) is selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH) in a patient.

Also provided are methods for the treatment of PAH in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH in a patient in need thereof, comprising administering to the patient Compound 1 via a titration scheme as disclosed herein.

Also provided are methods for the treatment of idiopathic PAH in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of idiopathic PAH in a patient in need thereof, comprising administering to the patient Compound 1 via a titration scheme as disclosed herein.

Also provided are methods for the treatment of familial PAH in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of familial PAH in a patient in need thereof, comprising administering to the patient Compound 1 via a titration scheme as disclosed herein.

Also provided are methods for the treatment of PAH associated with a collagen vascular disease in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with a collagen vascular disease in a patient in need thereof, comprising administering to the patient Compound 1 via a titration scheme as disclosed herein.

Also provided are methods for the treatment of PAH associated with a collagen vascular disease selected from: scleroderma. CREST syndrome, systemic lupus erythematosus (SLE), rheumatoid arthritis, Takayasu's arteritis, polymyositis, and dermatomyositis in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with a collagen vascular disease selected from: scleroderma, CREST syndrome, systemic lupus erythematosus (SEE), rheumatoid arthritis, Takayasu's arteritis, polymyositis, and dermatomyositis in a patient in need thereof, comprising administering to the patient Compound 1 via a titration scheme as disclosed herein.

Also provided are methods for the treatment of PAH associated with a congenital heart disease in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with a congenital heart disease in a patient in need thereof, comprising administering to the patient Compound 1 via a titration scheme as disclosed herein.

Also provided are methods for the treatment of PAH associated with a congenital heart disease selected from: atrial septic defect (ASD), ventricular septic defect (VSD) and patent ductus arteriosus in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with a congenital heart disease selected from: atrial septic defect (ASD), ventricular septic defect (VSD) and patent ductus arteriosus in a patient in need thereof, comprising administering to the patient Compound 1 via a titration scheme as disclosed herein.

Also provided are methods for the treatment of PAH associated with portal hypertension in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with portal hypertension in a patient in need thereof, comprising administering to the patient Compound 1 via a titration scheme as disclosed herein.

Also provided are methods for the treatment of PAH associated with HIV infection in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with HIV infection in a patient in need thereof, comprising administering to the patient Compound 1 via a titration scheme as disclosed herein.

Also provided are methods for the treatment of PAH associated with ingestion of a drug or toxin in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with ingestion of a drug or toxin in a patient in need thereof, comprising administering to the patient Compound 1 via a titration scheme as disclosed herein.

Also provided are methods for the treatment of PAH associated with hereditary hemorrhagic telangiectasia in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with hereditary hemorrhagic telangiectasia in a patient in need thereof, comprising administering to the patient Compound 1 via a titration scheme as disclosed herein.

Also provided are methods for the treatment of PAH associated with splenectomy in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with splenectomy in a patient in need thereof, comprising administering to the patient Compound 1 via a titration scheme as disclosed herein.

Also provided are methods for the treatment of PAH associated with significant venous or capillary involvement in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with significant venous or capillary involvement in a patient in need thereof, comprising administering to the patient Compound 1 via a titration scheme as disclosed herein.

Also provided are methods for the treatment of PAH associated with pulmonary veno-occlusive disease (PVOD) in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are to methods for tire treatment of PAH associated with pulmonary veno-occlusive disease (PVOD) in a patient in need thereof, comprising administering to the patient Compound 1 via a titration scheme as disclosed herein.

Also provided are methods for the treatment of PAH associated with pulmonary capillary hemangiomatosis (PCH) in a patient in need thereof, comprising prescribing and/or administering to the patient Compound 1 or a pharmaceutically acceptable salt, hydrate or solvate thereof, or a pharmaceutical composition thereof, via a titration scheme as disclosed herein. Also provided are methods for the treatment of PAH associated with pulmonary capillary hemangiomatosis (PCH) in a patient in need thereof, comprising administering to the patient Compound 1 via a titration scheme as disclosed herein.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.01 mg of Compound 1 once daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.01 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.02 mg of Compound 1 twice daily, in some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.03 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.04 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.06 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.08 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.1 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.2 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.3 mg of Compound 1 twice daily.

In some embodiments of the methods for the treatment of PAH in a patient in need thereof disclosed herein, comprising prescribing and/or administering to the patient Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.6 mg of Compound 1 twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.01 mg of Compound 1, once daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.01 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.02 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.03 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.04 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.06 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.08 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.1 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.2 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.3 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.6 mg of Compound 1, twice daily.

In some embodiments provided herein is a method for the treatment of PAH, the method comprising prescribing and/or administering to the patient a pharmaceutical composition comprising an amount of Compound 1, or a pharmaceutically acceptable salt, hydrate, or solvate thereof, equivalent to 0.01 mg to 0.6 mg of Compound 1, twice daily, such as 0.01 mg to 0.3 mg of Compound 1, twice daily, such as 0.01 mg to 0.2 mg of Compound 1, twice daily, such as 0.01 mg to 0.1 mg of Compound 1, twice daily, such as 0.02 mg to 0.08 mg of Compound 1, twice daily, such as 0.03 mg to 00.6 mg of Compound 1, twice daily, such as such as 0.04 mg of Compound 1 twice daily.

In some embodiments of the methods for the treatment of PAH, the Compound 1, or a pharmaceutically acceptable salt, hydrate, or solvate thereof, is formulated as a capsule or tablet suitable for oral administration. In some embodiments, the Compound 1, or a pharmaceutically acceptable salt, hydrate, or solvate thereof, is formulated as a capsule. In some embodiments, the Compound 1, or a pharmaceutically acceptable salt, hydrate, or solvate thereof, is formulated as a tablet.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.01 mg of Compound 1, once daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.01 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.02 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated wash HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.03 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), tire method comprising prescribing and/or administering to the patient a pharmaceutical composition comprising an amount of Compound 1, or a pharmaceutically acceptable salt, hydrate, or solvate thereof, equivalent to 0.04 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.06 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.08 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.1 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.2 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.3 mg of Compound 1, twice daily.

In some embodiments provided herein is a method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the method comprising prescribing and/or administering to the patient a pharmaceutical composition comprising an amount of Compound 1, or a pharmaceutically acceptable salt, hydrate, or solvate thereof, equivalent to 0.6 mg of Compound 1, twice daily.

In some embodiments of the methods for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the Compound 1, or a pharmaceutically acceptable salt, hydrate, or solvate thereof, is formulated as a capsule or tablet suitable for oral administration. In some embodiments, the Compound 1, or a pharmaceutically acceptable salt, hydrate, or solvate thereof, is formulated as a capsule. In some embodiments, the Compound 1, or a pharmaceutically acceptable salt, hydrate, or solvate thereof, is formulated as a tablet.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.01 mg of Compound 1, once daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.01 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.02 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.03 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.04 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.06 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.08 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.1 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.2 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.3 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.6 mg of Compound 1, twice daily.

Also provided is the use of Compound 1, or a pharmaceutically acceptable salt, hydrate, or solvate thereof, as described herein, in the manufacture of a medicament for the treatment of PAH, comprising prescribing and/or administering to the patient a pharmaceutical composition comprising an amount of Compound 1, or a pharmaceutically acceptable salt, hydrate, or solvate thereof, equivalent to 0.01 mg to 0.6 mg of Compound 1, twice daily, such as 0.01 mg to 0.3 mg of Compound 1, twice daily, such as 0.01 mg to 0.2 mg of Compound 1, twice daily, such as 0.01 mg to 0.1 mg of Compound 1, twice daily, such as 0.02 mg to 0.08 mg of Compound 1, twice daily, such as 0.03 mg to 0.06 mg of Compound 1, twice daily, such as such as 0.04 mg of Compound 1 twice daily.

In some embodiments of the methods for the treatment of PAH, the Compound 1, or a pharmaceutically acceptable salt, hydrate, or solvate thereof, is formulated as a capsule or tablet suitable for oral administration, in some embodiments, the Compound 1, or a pharmaceutically acceptable salt, hydrate, or solvate thereof, is formulated as a capsule, in some embodiments, the Compound 1, or a pharmaceutically acceptable salt, hydrate, or solvate thereof, is formulated as a tablet.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection;

PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.01 mg of Compound 1, once daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.01 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.02 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.03 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.04 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical, composition comprising an amount of Compound 1, or a pharmaceutically acceptable salt, hydrate, or solvate thereof, equivalent to 0.06 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.08 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.5 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.2 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.3 mg of Compound 1, twice daily.

Also provided is the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), comprising prescribing and/or administering to the patient a pharmaceutical composition comprising an amount of Compound 1, or a pharmaceutically acceptable salt, hydrate, or solvate thereof, equivalent to 0.6 mg of Compound 1, twice daily.

In some embodiments of the use of Compound 1, or a pharmaceutically acceptable salt, hydrate, or solvate thereof, as described herein, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the Compound 1, or a pharmaceutically acceptable salt, hydrate, or solvate thereof, is formulated as a capsule or tablet suitable for oral administration, in some embodiments, the Compound 1, or a pharmaceutically acceptable salt, hydrate, or solvate thereof, is formulated as a capsule. In some embodiments, the Compound 1, or a pharmaceutically acceptable salt, hydrate, or solvate thereof, is formulated as a tablet.

In some embodiments of the pharmaceutical composition or of the method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVQD); and PAH associated with pulmonary capillary hemangiomatosis (PCH), the dose of Compound 1, or a pharmaceutically acceptable salt, hydrate, or solvate thereof, is effective in in producing a difference of at least about 40 meters in 6MWD relative to the 6MWD prior to administration of the dose.

In some embodiments of the pharmaceutical composition or of the method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the dose of Compound 1, or a pharmaceutically acceptable salt, hydrate, or solvate thereof, is effective in producing a difference of at least about 45 meters in 6MWD relative to the 6MWD prior to administration of the dose.

In some embodiments of the pharmaceutical composition or of the method for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in a patient; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH), the dose of Compound 1, or a pharmaceutically acceptable salt, hydrate, or solvate thereof, is effective in producing a difference of at least about 50 meters in 6MWD relative to the 6MWD prior to administration of the dose.

As used herein "6MWD" refers to "six-minute walk distance", that is, the distance that the patient covers by walking for a six-minute period. In some embodiments, the 6MWD is the distance that the patient covers by walking for a six-minute period along an indoor surface. In some embodiments, the 6MWD is the distance that the patient covers by walking for a six-minute period along a flat indoor surface that is about 15 to about 50 meters in length, turning around every time the patient reaches a preset turnaround point on the surface.

In some embodiments, the 6MWD is determined according to the American Thoracic Society guidelines for the Six-minute Walk Test ("6MWT") disclosed in *Am. J Respir. Crit. Care Med* Vol. 166, p. 111-117, 2002; DOI: 10.1164/rccm.166/1/111, incorporated by reference herein in its entirety; also available at https://www.thoracic.org/statements/resources/pfet/sixminute.pdf.

In some embodiments of the 6MWD, equipment that may be used or present in the vicinity may include $O_2$ saturation equipment and forehead probes; a countdown timer or stopwatch; a mechanical lap counter; two small cones to mark the turnaround points; a chair that can be moved along the walking course; worksheets; a source of oxygen; a telephone; and an automated electronic defibrillator. The subject may prepare for the 6MWT by wearing comfortable clothing and appropriate shoes for walking; using any walking aids during the test, such as a cane or a walker; continuing any medical regimen including taking Compound 1 before the commencement of the 6MWT; eating alight meal before early morning or early afternoon 6MWTs; and avoiding vigorous exercise within 2 hours of beginning the test. Prior to the test the subject may sit at rest in a chair located near the starting position, for at least 10 minutes. Information that may be recorded includes one or more of the following: starting location, length of hallway, direction the subject walks, time of test, and subject's general condition.

The 6MWT may be immediately stopped for reasons that include the following: (1) chest pain, (2) intolerable dyspnea, (3) leg cramps, (4) staggering, (5) diaphoresis, and (6) pale or ashen appearance. Subjects who require supplemental oxygen must breathe a stable oxygen dose for at least 15 minutes prior to the measurement of $O_2$ saturation and until the end of the 6MWT. Absolute contraindications for the 6MWT include the following: unstable angina during the previous month and myocardial infarction during the previous month. Relative contraindications include a resting HR of more than 120, a sBP of more them 180 mmHg, and a dBP of more than 100 mmHg.

Also provided is the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound Lora pharmaceutically acceptable salt, hydrate, or solvate thereof, as described herein, in the manufacture of a medicament for the treatment of PAH, the treatment comprising administering Compound 1 via a titration scheme as disclosed herein.

Also provided is the use of a Compound 1, or a pharmaceutically acceptable salt, hydrate, or solvate thereof, as described herein, in the manufacture of a medicament for the treatment of idiopathic PAH, the treatment comprising prescribing and/or administering Compound 1 or a pharmaceutically acceptable salt, hydrate or solvate thereof, or a pharmaceutical composition thereof, via a titration scheme as disclosed herein. Also provided is the use of a Compound 1, or a pharmaceutically acceptable salt, hydrate, or solvate thereof, as described herein, in the manufacture of a medicament for the treatment of idiopathic PAH, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of familial PAH, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of familial PAH, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with a collagen vascular disease, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with a collagen vascular disease, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with a congenital heart disease, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with a congenital heart disease, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with a congenital heart disease selected from: atrial septic defect (ASD), ventricular septic defect (VSD) and patent ductus arteriosus, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with a congenital heart disease selected from: atrial septic defect (ASD), ventricular septic defect (VSD) and patent ductus arteriosus, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with portal hypertension, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with portal hypertension, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with HIV infection, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with HIV infection, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with ingestion of a drug or toxin, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with ingestion of a drug or toxin, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with hereditary hemorrhagic telangiectasia, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with hereditary hemorrhagic telangiectasia, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with splenectomy, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with splenectomy, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with significant venous or capillary involvement, the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with significant venous or capillary involvement, the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with pulmonary veno-occlusive disease (PVQD), the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with pulmonary veno-occlusive disease (PVOD), the treatment comprising administering Compound 1 via a titration scheme as disclosed herein.

Also provided is the use of Compound 1, or a pharmaceutically acceptable salt, hydrate, or solvate thereof, as described herein, in the manufacture of a medicament for the treatment of PAH associated with pulmonary capillary hemangiomatosis (PCH), the treatment comprising prescribing and/or administering Compound 1 or a pharmaceutically acceptable salt, hydrate or solvate thereof, or a pharmaceutical composition thereof, via a titration scheme as disclosed herein. Also provided is the use of Compound 1, or a pharmaceutically acceptable salt, hydrate, or solvate thereof, as described herein, in the manufacture of a medicament for the treatment of PAH associated with pulmonary capillary hemangiomatosis (PCH), the treatment comprising administering Compound 1 via a titration scheme as disclosed herein.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.01 mg of Compound 1 once daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.01 mg of Compound 1 twice daily.

In some embodiments of the use of Compound 1, or a pharmaceutically acceptable salt-hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.02 mg of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.03 mg of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.04 mg of Compound 1 twice daily.

In some embodiments of the use of Compound 1, or a pharmaceutically acceptable salt-hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.06 mg of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.08 mg of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.1 mg of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.2 mg of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.3 rug of Compound 1 twice daily.

In some embodiments of the use of Compound 1, or a pharmaceutically acceptable salt, hydrate, or solvate thereof, as described herein, in the manufacture of a medicament for the treatment of PAH, the treatment comprising prescribing and/or administering Compound 1 or a pharmaceutically acceptable salt, hydrate or solvate thereof, or a pharmaceutical composition thereof, via a titration scheme as disclosed herein, the optimized dose of Compound 1, or a pharmaceutically acceptable salt, hydrate, or solvate thereof, is equivalent to 0.6 mg of Compound 1 twice daily.

Also provided is Compound 1, or a pharmaceutically acceptable salt, hydrate, or solvate thereof, as described herein, for use in a method of treatment of PAH, the method comprising prescribing and/or administering Compound 1 or a pharmaceutically acceptable salt, hydrate or solvate thereof, or a pharmaceutical composition thereof, via a titration scheme as disclosed herein.

Also provided is Compound 1, or a pharmaceutically acceptable salt, hydrate, or solvate thereof, as described herein, for use in a method of treatment of PAH, the method comprising administering Compound 1 via a titration scheme as disclosed herein.

Also provided is Compound 1, or a pharmaceutically acceptable salt, hydrate, or solvate thereof, as described herein, for use in a method of treatment of idiopathic PAH, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of idiopathic PAH, the method comprising administering Compound 1 via a titration scheme as disclosed herein.

Also provided is Compound 1, or a pharmaceutically acceptable salt, hydrate, or solvate thereof, as described herein, for use in a method of treatment of familial PAH, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of familial PAH, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with a collagen vascular disease, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with a collagen vascular disease, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with a congenital heart disease, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with a congenital heart disease, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with a congenital heart disease selected from: atrial septic defect (ASD), ventricular septic defect (VSD) and patent ductus arteriosus, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with a congenital heart disease selected from: atrial septic defect (ASD), ventricular septic defect (VSD) and patent ductus arteriosus, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with portal hypertension, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with portal hypertension, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with HIV infection, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with HIV infection, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with ingestion of a drug or toxin, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with ingestion of a drug or toxin, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with hereditary hemorrhagic telangiectasia, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with hereditary hemorrhagic telangiectasia, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with splenectomy, the method comprising prescribing and/or administering Compound 3 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with splenectomy, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with significant venous or capillary involvement, the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with significant venous or capillary involvement, the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with pulmonary veno-occlusive disease (PVOD), the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with pulmonary veno-occlusive disease (PVOD), the method comprising administering Compound 1 via a titration scheme as disclosed herein.

Also provided is Compound 1, or a pharmaceutically acceptable salt, hydrate, or solvate thereof, as described herein, for use in a method of treatment of PAH associated with pulmonary capillary hemangiomatosis (PCH), the method comprising prescribing and/or administering Compound 1 or a pharmaceutically acceptable salt, hydrate or solvate thereof, or a pharmaceutical composition thereof, via a titration scheme as disclosed herein. Also provided is Compound 1, or a pharmaceutically acceptable salt, hydrate, or solvate thereof, as described herein, for use in a method of treatment of PAH associated with pulmonary capillary hemangiomatosis (PCH), the method comprising administering Compound 1 via a titration scheme as disclosed herein.

In some embodiments provided herein is a method of treating pulmonary arterial hypertension comprising
- prescribing and/or administering to a patient in need thereof Compound 1, or a
- pharmaceutically acceptable salt, hydrate, or solvate thereof, at an initial dose as disclosed herein;
- administering Compound 1, or a pharmaceutically acceptable salt, hydrate, or solvate thereof, via a titration scheme as disclosed herein until an optimized dose is administered; and
prescribing or administering the optimized dose twice daily to the patient for about 13 weeks.

In some embodiments provided herein is a method of treating pulmonary arterial hypertension comprising
- prescribing and/or administering to a patient in need thereof Compound 1, or a pharmaceutically acceptable salt, hydrate, or solvate thereof, at an initial dose as disclosed herein;
- administering Compound 1, or a pharmaceutically acceptable salt, hydrate, or solvate thereof, via a titration scheme as disclosed herein until an optimized dose is administered; and
- prescribing or administering the optimized dose twice daily to the patient for about 13 weeks to produce a difference of at least about 40 meters in 6MWD by the patient relative to the 6MWD prior to administration of the initial dose.

In some embodiments provided herein is a method of treating pulmonary arterial hypertension comprising
- prescribing and/or administering to a patient in need thereof Compound 1, or a pharmaceutically acceptable salt, hydrate, or solvate thereof, at an initial dose as disclosed herein;

administering Compound 1, or a pharmaceutically acceptable salt, hydrate, or solvate thereof, via a titration scheme as disclosed herein until an optimized dose is administered; and prescribing or administering the optimized dose twice daily to the patient for about 13 weeks to produce a difference of at least about 45 meters in 6MWD by the patient relative to the 6MWD prior to administration of the initial dose.

In some embodiments provided herein is a method of treating pulmonary arterial hypertension comprising prescribing and/or administering to a patient in need thereof Compound 1, or a pharmaceutically acceptable salt, hydrate, or solvate thereof, at an initial dose as disclosed herein;

administering Compound 1, or a pharmaceutically acceptable salt, hydrate, or solvate thereof, via a titration scheme as disclosed herein until an optimized dose is administered; and prescribing or administering the optimized dose twice daily to the patient for about 13 weeks to produce a difference of at least about 50 meters in 6MWD by the patient relative to the 6MWD prior to administration of the initial dose.

In some embodiments provided herein is a method of treating pulmonary arterial hypertension comprising prescribing and/or administering to a patient in need thereof Compound 1, or a pharmaceutically acceptable salt, hydrate, or solvate thereof, at an initial dose as disclosed herein;

administering Compound 1, or a pharmaceutically acceptable salt, hydrate, or solvate thereof, via a titration scheme as disclosed herein until an optimized dose is administered; and prescribing or administering the optimized dose twice daily to the patient for a time sufficient to produce a difference of at least about 40 meters in 6MWD by the patient relative to the 6MWD prior to administration of the initial dose.

In some embodiments provided herein is a method of treating pulmonary arterial hypertension comprising prescribing and/or administering to a patient in need thereof Compound 1, or a pharmaceutically acceptable salt, hydrate, or solvate thereof, at an initial dose as disclosed herein;

administering Compound 1, or a pharmaceutically acceptable salt, hydrate, or solvate thereof, via a titration scheme as disclosed herein until an optimized dose is administered; and prescribing or administering the optimized dose twice daily to the patient for a time sufficient to produce a difference of at least about 45 meters in 6MWD by tire patient relative to the 6MWD prior to administration of the initial dose.

In some embodiments provided herein is a method of treating pulmonary arterial hypertension comprising prescribing and/or administering to a patient in need thereof Compound 1, or a pharmaceutically acceptable salt, hydrate, or solvate thereof, at an initial dose as disclosed herein;

administering Compound 1, or a pharmaceutically acceptable salt, hydrate, or solvate thereof, via a titration scheme as disclosed herein until an optimized dose is administered; and prescribing or administering the optimized dose twice daily to the patient for a time sufficient to produce a difference of at least about 50 meters in 6MWD by the patient relative to the 6MWD prior to administration of the initial dose.

In some embodiments provided herein is a method of treating pulmonary arterial hypertension comprising prescribing and/or administering to a patient in need thereof Compound 1, or a pharmaceutically acceptable salt, hydrate, or solvate thereof, at an initial dose as disclosed herein; and administering Compound 1, or a pharmaceutically acceptable salt, hydrate, or solvate thereof, via a titration scheme as disclosed herein until an optimized dose is administered, the titration scheme comprises the up-titration of Compound 1, or a pharmaceutically acceptable salt, hydrate, or solvate thereof, over a period of no more than about nine weeks until the optimized dose is administered.

Also provided is a titration package for enabling compliance with a regimen of changing dosage of medication over a period of time, wherein the medication is Compound 1, or a pharmaceutically acceptable salt, hydrate, or solvate thereof, the package comprising:

a backing having an array of receivers, said array including a plurality of columns aid a plurality of rows;

a plurality of sets of solid dosage forms, each solid dosage form in a set having a common dose of the medication and a different dose than a solid dosage form of a different set, each set being disposed in receivers of one of an adjacent row and an adjacent column; different sets of solid dosage forms are disposed in different rows, each row being indicated as a successive time period, each column being indicated as a different day of the time period, sets of solid dosage forms having increased doses being disposed in receivers of rows indicated as successive time periods; and indicia disposed adjacent the columns and rows for displaying common days and successive time periods.

In some embodiments of the titration package, a plurality of doses of 0.01 mg each is disposed in receivers of a first row.

In some embodiments of the titration package, a plurality of doses of 0.02 mg each is disposed in receivers of a second row.

In some embodiments of the titration package, a plurality of doses of 0.03 mg each is disposed in receivers of a third row.

In some embodiments of the titration package, a plurality of doses of 0.04 mg each is disposed in receivers of a fourth row.

In some embodiments of the titration package, a plurality of doses of 0.06 mg each is disposed in receivers of a fifth row.

In some embodiments of the titration package, a plurality of doses of 0.08 mg each is disposed in receivers of a sixth row.

In some embodiments of the titration package, a plurality of doses of 0.1 mg each is disposed in receivers of a seventh row.

In some embodiments of the titration package, a plurality of doses of 0.2 mg each is disposed in receivers of an eighth row.

In some embodiments of the titration package, a plurality of doses of 0.3 mg each is disposed in receivers of a ninth row.

In some embodiments of the titration package, a plurality of doses of 0.6 mg each is disposed in receivers of a tenth row.

In some embodiments of the titration package, a plurality of doses of 0.01 mg each is disposed in receivers of a first row.

In some embodiments of the titration package, a plurality of doses of 0.01 mg each is disposed in receivers of a second row, wherein the number of doses disposed in the receivers of the second row is twice the number of doses disposed in the receivers of the second row.

In some embodiments of the titration package, a plurality of doses of 0.02 mg each is disposed in receivers of a third row.

In some embodiments of the titration package, a plurality of doses of 0.03 mg each is disposed in receivers of a fourth row.

In some embodiments of the titration package, a plurality of doses of 0.04 mg each is disposed in receivers of a fifth row.

In some embodiments of the titration package, a plurality of doses of 0.06 mg each is disposed in receivers of a sixth row.

In some embodiments of the titration package, a plurality of doses of 0.08 mg each is disposed in receivers of a seventh row.

In some embodiments of the titration package, a plurality of doses of 0.1 mg each is disposed in receivers of an eighth row.

In some embodiments of the titration package, a plurality of doses of 0.2 mg each is disposed in receivers of a ninth row.

In some embodiments of the titration package, a plurality of doses of 0.3 mg each is disposed in receivers of a tenth row.

In some embodiments of the titration package, a plurality of doses of 0.6 mg each is disposed in receivers of an eleventh row.

In some embodiments of the titration package, each tune period is about one week.

Also provided is a method of "combination" therapy comprising prescribing and/or administering Compound 1, or a pharmaceutically acceptable salt, solvate, or hydrate thereof, in combination with at least one known pharmaceutical agent. Also provided is a method of "combination" therapy comprising prescribing and/or administering Compound 1, or a pharmaceutically acceptable salt, solvate, or hydrate thereof, in combination with at least one known pharmaceutical agent as described herein and a pharmaceutically acceptable carrier. As used herein, "combination" as used in reference to drug combinations and/or combinations of Compound 1, or a pharmaceutically acceptable salt, solvate, or hydrate thereof, with at least one additional pharmaceutical agent refers to (1) a product comprised of two or more components, i.e., drug/device, biologic/device, drug/biologic, or drug/device/biologic, that are physically, chemically, or otherwise combined or mixed and produced as a single entity-; (2) two or more separate products packaged together in a single package or as a unit and comprised of drug and device products, device and biological products, or biological and drug products; (3) a drug, device, or biological product packaged separately that according to its investigational plan or proposed labeling is intended for use only with an approved individually specified drug, device, or biological product where both are required to achieve the intended use, indication, or effect and where upon approval of the proposed product the labeling of the approved product would need to be changed, e.g., to reflect a change in intended use, dosage form, strength, route of administration, or significant change in dose; or (4) any investigational drug, device, or biological product packaged separately that according to its proposed labeling is for use only with another individually specified investigational drug, device, or biological product where both are required to achieve the intended use, indication, or effect. Combinations include without limitation a fixed-dose combination product (FDC) in which two or more separate drug components are combined in a single dosage form; a co-packaged product comprising two or more separate drug products in their final dosage forms, packaged together with appropriate labeling to support the combination use; and an adjunctive therapy in which a patient is maintained on a second drug product that is used together with (i.e., in adjunct to) the primary treatment, although tire relative doses are not fixed, and the drags or biologics are not necessarily given at the same time. Adjunctive therapy products may be co-packaged, and may or may not be labeled for concomitant use.

In some embodiments, Compound 1, or a pharmaceutically acceptable salt, solvate, or hydrate thereof is administered in combination with thrombolytic therapy, for example, tissue-type plasminogen activator (t-PA), to provide cardioprotection following Ml or postischemic myocardial dysfunction or protection from ischemic injury during percutaneous coronary intervention, and the like, including complications resulting therefrom. PGI2 receptor agonists can also be used in antiplatelet therapies in combination with, for example, alpha-tocopherol (vitamin E), echistatin (a disintegrin) or, in states of hypercoaguability, heparin. (See, e.g., Chan., J. Nutr., 1998, 128:1593-1596; Mardla et al. Platelets, 2004, 15:319-324; Bernabei et al., Ann. Thorac. Surg., 1995, 59:149-153; Gainza et al. J. Nephrol., 2006, 19:648-655.)

In some embodiments. Compound 1, or a pharmaceutically acceptable salt, solvate, or hydrate thereof, is administered together with at least one pharmaceutical agent known to prevent and/or treat one or more of the adverse effects described herein.

In some embodiments, the at least one pharmaceutical agent is an agent for thrombolytic therapy. In some embodiments, Compound 1, or a pharmaceutically acceptable salt, solvate, or hydrate thereof and the agent for thrombolytic therapy are formulated as a fixed dose combination product. In some embodiments. Compound 1, or a pharmaceutically acceptable salt, solvate, or hydrate thereof and the agent for thrombolytic therapy are formulated as a co-packaged product, in some embodiments, the Compound 1, or a pharmaceutically acceptable salt, solvate, or hydrate thereof and the agent for thrombolytic therapy are formulated for adjunctive therapy.

In some embodiments, the at least one pharmaceutical agent is tissue-type plasminogen activator. In some embodiments, Compound 1, or a pharmaceutically acceptable salt, solvate, or hydrate thereof and the tissue-type plasminogen activator are formulated as a fixed dose combination product. In some embodiments, Compound 1, or a pharmaceutically acceptable salt, solvate, or hydrate thereof and the tissue-type plasminogen activator are formulated as a co-packaged product. In some embodiments, the Compound 1, or a pharmaceutically acceptable salt, solvate, or hydrate thereof and the tissue-type plasminogen activator are formulated for adjunctive therapy.

In some embodiments, the at least one pharmaceutical agent is an agent for antiplatelet therapy. In some embodiments, Compound 1, or a pharmaceutically acceptable salt, solvate, or hydrate thereof and the agent for antiplatelet therapy are formulated as a fixed dose combination product. In some embodiments, Compound 1, or a pharmaceutically acceptable salt, solvate, or hydrate thereof and the agent for antiplatelet therapy are formulated as a co-packaged product. In some embodiments, the Compound 1, or a pharmaceutically acceptable salt, solvate, or hydrate thereof and the agent for antiplatelet therapy are formulated for adjunctive therapy.

In some embodiments, the at least one pharmaceutical agent is an agent for antiplatelet therapy. In some embodiments, Compound 1, or a pharmaceutically acceptable salt, solvate, or hydrate thereof and the agent for antiplatelet therapy are formulated as a fixed dose combination product. In some embodiments, Compound 1, or a pharmaceutically acceptable salt, solvate, or hydrate thereof and the agent for antiplatelet therapy are formulated as a co-packaged product. In some embodiments, the Compound 1, or a pharmaceutically acceptable salt, solvate, or hydrate thereof and the agent for antiplatelet therapy are formulated for adjunctive therapy.

In some embodiments, the at least one pharmaceutical agent is alpha-tocopherol. In some embodiments, Compound 1, or a pharmaceutically acceptable salt, solvate, or hydrate thereof and the alpha-tocopherol are formulated as a fixed dose combination product. In some embodiments, Compound 1, or a pharmaceutically acceptable salt, solvate, or hydrate thereof and the alpha-tocopherol are formulated as a co-packaged product. In some embodiments, the Compound 1, or a pharmaceutically acceptable salt, solvate, or hydrate thereof and the alpha-tocopherol are formulated for adjunctive therapy.

In some embodiments, the at least one pharmaceutical agent is echistatin. In some embodiments, Compound 1, or a pharmaceutically acceptable salt, solvate, or hydrate thereof and the echistatin are formulated as a fixed dose combination product. In some embodiments, Compound 1, or a pharmaceutically acceptable salt, solvate, or hydrate thereof and the echistatin are formulated as a co-packaged product. In some embodiments, the Compound 1, or a pharmaceutically acceptable salt, solvate, or hydrate thereof and the echistatin are formulated for adjunctive therapy.

In some embodiments, the at least one pharmaceutical agent is heparin. In some embodiments, Compound 1, or a pharmaceutically acceptable salt, solvate, or hydrate thereof and the heparin are formulated as a fixed dose combination product. In some embodiments, Compound 1, or a pharmaceutically acceptable salt, solvate, or hydrate thereof and the heparin are formulated as a co-packaged product. In some embodiments, the Compound 1, or a pharmaceutically acceptable salt, solvate, or hydrate thereof and the heparin me formulated for adjunctive therapy.

In some embodiments, the at least one pharmaceutical agent is at least one pharmaceutical agent known to prevent and/or treat one or more of the adverse effects described herein. In some embodiments. Compound 1, or a pharmaceutically acceptable salt, solvate, or hydrate thereof and the at least one pharmaceutical agent known to prevent and/or treat one or more of the adverse effects described herein are formulated as a fixed dose combination product. In some embodiments, Compound 1, or a pharmaceutically acceptable salt, solvate, or hydrate thereof and the at least one pharmaceutical agent known to prevent and/or treat one or more of the adverse effects described herein are formulated as a co-packaged product. In some embodiments, the Compound 1, or a pharmaceutically acceptable salt, solvate, or hydrate thereof and the at least one pharmaceutical agent known to prevent and/or treat one or more of the adverse effects described herein are formulated for adjunctive therapy.

Also provided is a kit comprising a titration package as disclosed herein and instructions indicating that the medication is to be administered to a patient in need of treatment of pulmonary arterial hypertension.

Also provided is a method of treating pulmonary arterial hypertension comprising providing a titration package as disclosed herein to patient in need thereof.

In some embodiments. Compound 1 or a pharmaceutically acceptable salt, solvate or hydrate thereof is administered in a tablet or a capsule suitable for oral administration, in some embodiments, Compound 1 or a pharmaceutically acceptable salt, solvate or hydrate thereof is administered in a capsule suitable for oral administration.

Conventional excipients, such as binding agents, fillers, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound in a suitable liquid vehicle and filter sterilizing the solution before filling and sealing an appropriate vial or ampule. These are just a few examples of the many appropriate methods well known in the art for preparing dosage form s. Suitable pharmaceutically-acceptable carriers, outside those mentioned herein, are known in the art; for example, see Remington, *The Science and Practice of Pharmacy*, $20^{th}$ Edition, 2000, Lippincott Williams & Wilkins, (Editors: Gennaro et al.)

While it is possible that, for use in the prophylaxis or treatment, a compound can, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drag for absorption in an efficient manner with minimal degradation of the drag. Typically, transdermal patches comprise an impermeable backing layer, a single pressure sensitive adhesive and a removable protective layer with a release liner. One of ordinary skill in the art wall understand and appreciate the techniques appropriate for manufacturing a desired efficacious transdermal patch based upon the needs of the artisan.

The compounds provided herein, together with a conventional adjuvant, carrier, or diluent, can thus be placed into the form of pharmaceutical formulations and unit dosages thereof and in such form may be employed as solids, such as tablets or filled capsules, or liquids, such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. Tire active ingredient may also be administered by injection as a composition wherein, for example, saline, dextrose or water may be used as a suitable pharmaceutically acceptable carrier.

The compounds provided herein can be administered in a wide variety of oral and parenteral dosage forms. It will be obvious to those skilled in the art that the dosage forms may comprise, as the active component, either a compound provided herein or a pharmaceutically acceptable salt, solvate or hydrate of a compound provided herein.

Some embodiments include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

Further embodiments include the embodiment disclosed in the following Example, which is not to be construed as limiting in any way.

Example 1—Single Ascending Dose Study with Healthy Subjects

This study was a phase 1, randomized, double-blind, placebo-controlled study of four cohorts of 8 subjects each (2 subjects were assigned to receive placebo, and 6 to receive Compound 1). Each cohort was assigned to receive a single dose level of blinded study medication in an ascending dose fashion; dosing began at 0.1 mg.

All enrolled subjects received a single oral dose of study medication (Compound 1 or placebo). Dose escalation was slowed or discontinued when predefined safety criteria based on peak plasma exposure levels, blood pressure changes, or adverse events (AEs) were met. Dose escalation was discontinued based on AEs of prolonged nausea and vomiting that was severe in intensity experienced by subjects during the 2nd cohort (0.2 mg Compound 1). Two lower dose cohorts were added, in which the doses of Compound 1 were 0.05 mg and 0.03 respectively.

After each cohort was dosed, the following safety parameters were monitored: vital signs, clinical laboratory tests to include serum chemistry, hematology, and urinalysis, 12-lead ECG, plasma Compound 1 concentration, and AEs. Pharmacokinetic parameters-were monitored and calculated for Compound 1.

Adverse Events

A summary of the adverse events observed in tins study is shown in table 1.

TABLE 1 a) Summary of adverse events

| | Placebo | 0.03 mg | 0.05 mg | 0.1 mg | 0.2 mg |
|---|---|---|---|---|---|
| No. of subjects | 8 | 6 | 6 | 6 | 6 |
| No. of subjects reporting AEs | 3 | 2 | 5 | 6 | 6 |
| Photophobia | 0 | 0 | 1 | 0 | 0 |
| Nausea | 0 | 0 | 1 | 2 | 3 |
| Vomiting | 0 | 0 | 0 | 2 | 6 |
| Abdominal pain | 0 | 0 | 1 | 1 | 0 |
| Diarrhoea | 0 | 0 | 0 | 0 | 1 |
| Jaw pain | 0 | 0 | 2 | 3 | 1 |
| Neck pain | 0 | 0 | 0 | 1 | 0 |

TABLE 1-continued

| | | | | | |
|---|---|---|---|---|---|
| Muscle spasm | 0 | 0 | 0 | 0 | 1 |
| Pain in extremity | 0 | 0 | 0 | 0 | 1 |
| Headache | 3 | 2 | 5 | 5 | 5 |
| Dizziness | 0 | 0 | 0 | 1 | 0 |
| Cough | 1 | 0 | 0 | 0 | 0 |
| Oropharyngeal pain | 0 | 0 | 0 | 0 | 1 |
| Flushing | 0 | 0 | 1 | 1 | 2 |

At each level of summarization in Table 1a), subjects reporting more than one event were only counted once b) Number of Subjects Reporting AEs By Most Direct Relationship to Study Treatment

| | Placebo | 0.03 mg | 0.05 mg | 0.1 mg | 0.2 mg |
|---|---|---|---|---|---|
| Probably related | 0 | 0 | 0 | 1 | 6 |
| Possibly related | 1 | 2 | 5 | 4 | 0 |
| Probably not related | 0 | 0 | 0 | 0 | 0 |
| Definitely not related | 2 | 0 | 0 | 1 | 0 |

Example 2—Multiple Ascending Dose Study with Healthy Subjects

This study was a phase 1, randomized, double-blind, placebo-controlled, multiple-dose, dose titration study. A titration interval of 6 days was employed, with each dose being administered for at least 5 days. One goal was to determine the effect of dose titration on adverse effects.

In each of two subject cohorts, Cohort 1 aid Cohort 2, subjects were treated at each dose level for duration of 5 days with exception of the last dose level which included 7 days of treatment.

The protocol was amended to provide for an additional cohort, Cohort 3, in order to evaluate a different dose escalation regimen, as disclosed below.

Cohorts 1 and 2: Two groups of 15 subjects were enrolled and randomized to receive placebo (5 subjects per Cohort) or a starting dose of 0.05 mg Compound 1 (10 subjects per Cohort) on Day 1. Once daily (q.d.) dosing continued through 5 days. If tolerated, the next dose escalation (placebo or 0.1 mg q.d. Compound 1) occurred on Day 6 and this dose was administered daily through Day 10. Subsequent dose escalations were to occur in the same manner every 6th day for up to 3 additional dose escalations if tolerated (placebo or 0.2, 0.3, and 0.4 mg Compound 1) with the final dose maintained for a duration of 7 days. The dose could be decreased ("de-escalated") or increased ("re-escalated") based on assessment of safety and tolerability.

Cohort 3: One group of 25 subjects (5 placebo and 20 active) were enrolled and randomized to receive a starting dose of 0.01 mg Compound 1 twice daily or placebo on Day 1. Twice daily dosing continued through 5 days. If tolerated, the next dose escalation (placebo or Compound 1 0.02 mg twice daily) occurred on Day 6 and this dose was administered daily through Day 10. Subsequent dose escalations were to occur in the same manner every 6th day for up to 4 additional dose escalations if tolerated (placebo or 0.03, 0.04, 0.05, and 0.07 mg twice daily Compound 1). The dose could be decreased ("de-escalated") or increased ("re-escalated") based on assessment of safety and tolerability. The doses tested in this cohort were 0.01, 0.02, 0.03, 0.04, 0.05, and 0.07 mg administered twice daily for a total daily dose of 0.02, 0.04, 0.06, 0.08, 0.1, and 0.14 mg, respectively.

Compound 1 capsules were provided as 0.01 mg (alt Cohorts) and 0.1 mg (Cohorts 1 and 2 only) strengths.

In the single-ascending dose study of Example 1 above, the initial starting dose of 0.1 mg was tolerated but some subjects experienced nausea, vomiting, headache, and jaw pain. Intolerable AEs were experienced at the next dose level of 0.2 mg in that study. Accordingly, the starting dose in Cohorts 1 and 2 in this Example 2 the initial dose was 0.05 mg.

Adverse Events

In Cohorts 1 and 2, three (15%) subjects were unable to tolerate the starting dose of 0.05 mg once daily. Of these, 2 subjects were de-escalated to the lowest dose of 0.03 mg once daily for the remainder of the study; 1 of the subjects was able to subsequently re-escalate to 0.05 mg for the remainder of the study. One subject withdrew on Day 1 of the study One subject was able to escalate to 0.2 mg once daily, but was then de-escalated over time to 0.03 mg once daily by the remainder of the study. One subject tolerated the 0.2 mg once daily dose, and this same subject attained the highest dose administered to a study subject in Cohorts 1 and 2 at 0.4 mg once daily. However, the 0.4 mg once daily dose was not tolerated and the subject finished the remainder of the study at the 0.3 mg dose once daily.

In Cohort 3, all of the subjects were able to tolerate the starting dose of 0.01 mg twice daily and the first escalation to 0.02 mg twice daily Compound 1. Five subjects completed the study at the 0.03 mg twice daily dose. Two subjects were able to escalate to the 0.04 mg twice daily dose level through study completion. Five subjects were able to escalate to the 0.05 mg dose level through study completion. Two subjects were able to escalate to 0.07 mg twice daily, the highest dose level administered to a study subject in Cohort 3. This dose was tolerated through study completion. One subject discontinued treatment on Day 2.0 due to an adverse event.

For each cohort, the final daily dose of Compound 1 taken by subjects was as shown in Table 2 below:

TABLE 2

| Final Compound 1 Total Daily Dose mg) | |
|---|---|
| Cohorts 1 and 2 | Cohort 3 |
| 0.03 mg - 3 subjects | 0.04 mg - 4 subjects |
| 0.05 mg - 9 subjects | 0.06 mg - 6 subjects |
| 0.10 mg - 7 subjects | 0.08 mg - 2 subjects |
| 0.30 mg - 1 subject | 0.10 mg - 6 subjects |
| | 0.14 mg - 2 subjects |

The highest dose that a subject received for at least 3 days in either Cohort 1 and 2 or Cohort 3 was as shown in fable 3 below:

TABLE 3

| highest dose that a subject received for at least 3 days | |
|---|---|
| Cohorts 1 and 2 | Cohort 3 |
| 0.03 mg - 17 subjects | 0.04 mg - 20 subjects |
| 0.1 mg - 8 subjects | 0.04 mg - 20 subjects |
| 0.2 mg - 1 subjects | 0.06 mg - 19 subjects |
| 0.30 mg - 1 subject | 0.08 mg - 11 subjects |
| | 0.10 mg - 8 subjects |
| | 0.14 mg - 3 subjects |

A summary of the adverse events leading to a decrease of the dose of Compound 1 observed in Cohorts 1 and 2 is shown in table 4.

TABLE 4

| Adverse Events (no of subjects) leading to Decrease of Compound 1 Dose in Cohorts 1 and 2 | | | | | | | |
|---|---|---|---|---|---|---|---|
| | Placebo (N = 10) | Total (all doses) (N = 20) | 0.03 mg (N = 4) | 0.05 mg (N = 20) | 0.1 mg (N = 16) | 0.2 mg (N = 5) | 0.3 mg (N = 1) | 0.4 mg (N = 1) |
| Vomiting | 0 | 8 | 0 | 4 | 2 | 2 | 0 | 0 |
| Headache | 0 | 8 | 0 | 2 | 5 | 1 | 0 | 0 |
| Nausea | 0 | 4 | 0 | 1 | 1 | 2 | 0 | 0 |
| Diarrhoea | 0 | 1 | 0 | 1 | 0 | 0 | 0 | 0 |
| Chest pain | 0 | 1 | 0 | 0 | 1 | 0 | 0 | 0 |
| Jaw pain | 0 | 1 | 0 | 0 | 1 | 0 | 0 | 0 |
| Erythema | 0 | 1 | 0 | 0 | 0 | 0 | 0 | 1 |

At each level of summarization in Table 1a), subjects reporting more than one event were only counted once A summary of the adverse events leading to a decrease of the dose of Compound 1 observed in Cohort 3 is shown in table 5.

TABLE 5

| Adverse Events (no. of subjects) leading to Decrease of Compound 1 Dose in Cohort 3 | | | | | | | |
|---|---|---|---|---|---|---|---|
| | Placebo (N = 5) | Total (all doses) (N = 20) | 0.01 mg (N = 20) | 0.02 mg (N = 20) | 0.03 mg (N = 20) | 0.04 mg (N = 12) | 0.05 mg (N = 8) | 0.07 mg (N = 4) |
| Headache | 0 | 10 | 1 | 6 | 1 | 1 | 0 | 1 |
| Nausea | 0 | 5 | 0 | 3 | 1 | 0 | 0 | 1 |
| Myalgia | 0 | 4 | 1 | 2 | 1 | 0 | 0 | 0 |
| Dizziness | 0 | 3 | 0 | 0 | 0 | 2 | 1 | 0 |
| Abdominal pain | 0 | 2 | 0 | 0 | 1 | 0 | 1 | 0 |
| Diarrhoea | 0 | 2 | 0 | 1 | 1 | 0 | 0 | 0 |

TABLE 5-continued

Adverse Events (no. of subjects) leading to Decrease of Compound 1 Dose in Cohort 3

|  | Placebo (N = 5) | Total (all doses) (N = 20) | 0.01 mg (N = 20) | 0.02 mg (N = 20) | 0.03 mg (N = 20) | 0.04 mg (N = 12) | 0.05 mg (N = 8) | 0.07 mg (N = 4) |
|---|---|---|---|---|---|---|---|---|
| Arthralgia | 1 | 2 | 0 | 1 | 0 | 0 | 0 | 1 |
| Chest discomfort | 0 | 1 | 0 | 0 | 1 | 0 | 0 | 0 |
| Chest pain | 0 | 1 | 0 | 1 | 0 | 0 | 0 | 0 |
| Palpitations | 0 | 1 | 0 | 1 | 0 | 0 | 0 | 0 |
| Vomiting | 0 | 1 | 0 | 1 | 0 | 0 | 0 | 0 |
| Priapism | 0 | 1 | 0 | 0 | 1 | 0 | 0 | 0 |
| Jaw pain | 0 | 1 | 0 | 0 | 0 | 0 | 0 | 1 |

The majority of subjects, regardless of treatment group, experienced one or more APIs, Most of the AEs reported in the study were considered moderate in intensity (88%). Within the Compound 1 group, 95% of AEs were considered moderate in intensity and 90% were deemed by the investigator to be probably related to study drug.

Example 3—Administration of Compound 1 to Patients

A capsule containing an initial dose of 0.01 mg of Compound 1 is administered to a patient twice daily for one week. Tire patient is then evaluated by a health care practitioner to determine whether the patient tolerates the initial dose. If the patient does not tolerate the 0.01 mg initial dose, Compound 1 is not administered to the patient further. If the patient tolerates the initial dose, the dose is increased to 0.02 mg. A capsule containing tire increased dose of 0.02 mg of Compound 1 is administered to a patient twice daily for one week and the patient is again evaluated to determine whether the patient tolerates the dose. The cycle is repeated, further increasing the dose, according to the following schedule, provided that the patient continues to tolerate the increased or further increased, dose.

TABLE 6

Amount of Compound 1 (in mg) administered to the patient during each of nine weeks

|  | Week 1 | Week 2 | Week 3 | Week 4 | Week 5 | Week 6 | Week 7 | Week 8 | Week 9 |
|---|---|---|---|---|---|---|---|---|---|
| Dose | 0.01 | | | | | | | | |
| Increased Dose | | 0.02 | | | | | | | |
| Further Increased Dose | | | 0.03 | 0.04 | 0.06 | 0.08 | 0.1 | 0.2 | 0.3 |

If a dose is reached where the patient does not tolerate that dose, Compound 1 is not administered to the patient further. The optimized dose for that patient is the highest dose tolerated by that patient. As an example, a patient is administered 0.01 mg of Compound 1 twice daily on Week 1, 0.02 mg of Compound 1 twice daily on Week 2, 0.03 mg of Compound 1 twice daily on Week 3, and 0.04 mg of Compound 1 twice daily on Week 4, each time tolerating tire dose. The patient is administered 0.06 mg of Compound 1 twice daily on Week 5, and does not tolerate the 0.06 mg twice daily. The optimized dose for the patient is 0.04 mg of Compound 1 twice daily.

Example 4—Administration of Compound 1 to Patients

This study is conducted as a 22 week, randomized, double-blind, placebo controlled study which includes a dose titration period of up to 9 weeks. Patients are randomized 2:1 active to placebo.

Right Heart Catheterization (RHC) measurements are obtained prior to study Day 1 of the dose titration period and at Week 22. The following values are obtained and recorded: PAP (systolic, diastolic, and mean), HR, right atrial pressure (RAP), pulmonary capillary wedge pressure (PCWP) right ventricular pressure (RVP) and cardiac output (CO), pulmonary vascular resistance (PVR), arterial and mixed venous oxygen saturation, FiO2 (if applicable). Systemic vascular resistance (SVR) is estimated from blood pressure measurements.

The primary efficacy endpoints are: a) change from baseline in PVR after 22 weeks of treatment, and b) change from baseline in 6 MWD after 22 weeks of treatment. Efficacy is assessed in a stepwise manner: the statistical significance of Compound 1 versus placebo result is determined for the change from baseline in PVR at the end of 22 weeks of treatment. If the change from baseline in PVR is significant ($p<0.05$, two-sided), the change from baseline in 6MWD is then tested.

Compound 1 is administered as a hard-gelatin capsule formulation in 0.01, 0.02, 0.03, 0.04, and 0.10 mg dose strengths.

The starting dose of Compound 1 is 0.01 mg twice daily. The dose of Compound 1 is titrated according to patient tolerability. Available dosage forms include 0.01, 0.02, 0.03, 0.04 mg, and 0.10 mg.

If the initial dose is tolerated (0.01 mg twice daily), then the dose is increased once a week in the following fashion: 0.02 mg twice daily, 0.03 mg twice daily, 0.04 mg twice daily, 0.06 mg twice daily, 0.08 mg, 0.1 mg twice daily, 0.2 mg twice daily and 0.3 mg twice daily. The dose may be escalated to a possible maximum total daily dose of 0.6 mg (0.3 mg twice daily) pending tolerability.

If a dose is not tolerated, the study drug may be decreased to the previous dose level. If the initial dose of 0.01 mg twice daily is not tolerated, dosing may be decreased to 0.01 mg once daily.

In this example, the 6MWD is determined according to the following Six-minute Walk Test ("6MWT"):

The 6MWT is performed indoors along a long, flat, straight, hallway with a hard surface 15-50 meters in length having a preset starting line and turnaround points. If more than one test is performed, repeat testing is performed about the same time of day. Prior to the test the lap counter is set to 0 and the time to 6 minutes. The subject is instructed to walk as far as possible for 6 minutes by walking back and forth in the hallway, without running or jogging. The subject is instructed not to talk during the walk. The subject is notified at one-minute intervals of the time remaining in the 6MWT—thus, for example, the subject is notified after the first minute that there me five minutes remaining. When there are 15 seconds from completion of the 6MWT, the subject is notified that the subject is about to be told to stop walking. At the six-minute mark, as indicated (for example) by a buzzer, the subject is told to stop walking and the spot where the subject has stopped is marked with tape. The number of laps is recorded, and the number of meters in the final partial lap is recorded using a tape measure. The total distance walked is calculated, rounding to the nearest meter, and recorded.

Other uses of the disclosed methods will become apparent to those in the art based upon, inter alia, a review of this patent document.

What is claimed is:

1. A titration package for enabling compliance with a regimen of changing dosage of medication over a period of time, wherein the medication is 2-(((1r,4r)-4-(((4-chlorophenyl)(phenyl)carbarnoyloxy)methyl)cyclohexyl)methoxy) acetic acid (Compound 1), or a pharmaceutically acceptable salt, hydrate, or solvate thereof, the package comprising:
   a backing having an array of receivers, said array including a plurality of columns and a plurality of rows;
   a plurality of sets of solid dosage forms, each solid dosage form in a set having a common dose of the medication and a different dose than a solid dosage form of a different set, each set being disposed in receivers of one of an adjacent row and an adjacent column; different sets of solid dosage forms are disposed in different rows, each row being indicated as a successive time period, each column being indicated as a different day of the time period, sets of solid dosage forms having increased doses being disposed in receivers of rows indicated as successive time periods; and indicia disposed adjacent the columns and rows for displaying common days and successive time periods.

2. A kit comprising a titration package of claim 1 and instructions indicating that the medication is to be administered to a patient in need of treatment of pulmonary arterial hypertension.

3. A method of treating pulmonary arterial hypertension comprising providing a kit of claim 2 to patient in need thereof.

4. The titration package of claim 1, wherein the plurality of sets of solid dosage forms comprise one or more of the following sets:
   a set of solid dosage forms comprising an amount of Compound 1, or a pharmaceutically acceptable salt, hydrate, or solvate thereof, equivalent to 0.01 mg of Compound 1;
   a set of solid dosage forms comprising an amount of Compound 1, or a pharmaceutically acceptable salt, hydrate, or solvate thereof, equivalent to 0.02 mg of Compound 1;
   a set of solid dosage forms comprising an amount of Compound 1, or a pharmaceutically acceptable salt, hydrate, or solvate thereof, equivalent to 0.03 mg of Compound 1;
   a set of solid dosage forms comprising an amount of Compound 1, or a pharmaceutically acceptable salt, hydrate, or solvate thereof, equivalent to 0.04 mg of Compound 1;
   a set of solid dosage forms comprising an amount of Compound 1 or a pharmaceutically acceptable salt, hydrate, or solvate thereof, equivalent to 0.06 mg of Compound 1;
   a set of solid dosage forms comprising an amount of Compound 1, or a pharmaceutically acceptable salt, hydrate, or solvate thereof, equivalent to 0.08 mg of Compound 1;
   a set of solid dosage forms comprising an amount of Compound 1 or a pharmaceutically acceptable salt, hydrate, or solvate thereof, equivalent to 0.1 mg of Compound 1;
   a set of solid dosage forms comprising an amount of Compound 1, or a pharmaceutically acceptable salt, hydrate, or solvate thereof, equivalent to 0.2 mg of Compound 1;
   a set of solid dosage forms comprising an amount of Compound 1, or a pharmaceutically acceptable salt, hydrate, or solvate thereof, equivalent to 0.3 mg of Compound 1; and
   a set of solid dosage forms comprising an amount of Compound 1, or a pharmaceutically acceptable salt, hydrate, or solvate thereof, equivalent to 0.6 mg of Compound 1.

5. The titration package of claim 1, wherein the plurality of sets of solid dosage forms comprise an initial set of solid dosage forms comprising an amount of Compound 1, or a pharmaceutically acceptable salt, hydrate, or solvate thereof, equivalent to 0.05 mg of Compound 1 once daily in each receiver of the first row.

6. The titration package of claim 5, wherein the plurality of sets of solid dosage forms comprise a second set of solid dosage forms comprising an amount of Compound 1, or a pharmaceutically acceptable salt, hydrate, or solvate thereof, equivalent to 0.1 mg of Compound 1 once daily in each receiver of the second row.

7. The titration package of claim 5, wherein the amount of Compound 1, or a pharmaceutically acceptable salt, hydrate, or solvate thereof, increases by an amount equivalent to 0.05 mg of Compound 1 in each successive row.

8. The titration package of claim 1, wherein the plurality of sets of solid dosage forms comprise an initial set of solid dosage forms comprising 0.05 mg of Compound 1 once daily in each receiver of the first row.

9. The titration package of claim 8, wherein the plurality of sets of solid dosage forms comprise a second set of solid dosage forms comprising 0.1 mg of Compound 1 once daily in each receiver of the second row.

10. The titration package of claim 8, wherein the amount of Compound 1 increases by 0.05 mg of Compound 1 in each successive row.

11. The titration package of claim 8, wherein the initial set of solid dosage forms are configured to be administered for about a week, and each time period is about one week.

12. The kit of claim 2, wherein the plurality of sets of solid dosage forms comprise one or more of the following sets:
   a set of solid dosage forms comprising an amount of Compound 1, or a pharmaceutically acceptable salt, hydrate, or solvate thereof, equivalent to 0.01 mg of Compound 1;
   a set of solid dosage forms comprising an amount of Compound 1, or a pharmaceutically acceptable salt, hydrate, or solvate thereof, equivalent to 0.02 mg of Compound 1;

a set of solid dosage forms comprising an amount of Compound 1, or a pharmaceutically acceptable salt, hydrate, or solvate thereof, equivalent to 0.03 mg of Compound 1;

a set of solid dosage forms comprising an amount of Compound 1, or a pharmaceutically acceptable salt, hydrate, or solvate thereof, equivalent to 0.04 mg of Compound 1;

a set of solid dosage forms comprising an amount of Compound 1, or a pharmaceutically acceptable salt, hydrate, or solvate thereof, equivalent to 0.06 mg of Compound 1;

a set of solid dosage forms comprising an amount of Compound 1, or a pharmaceutically acceptable salt, hydrate, or solvate thereof, equivalent to 0.08 mg of Compound 1;

a set of solid dosage forms comprising an amount of Compound 1, or a pharmaceutically acceptable salt, hydrate, or solvate thereof, equivalent to 0.1 mg of Compound 1;

a set of solid dosage forms comprising an amount of Compound 1, or a pharmaceutically acceptable salt, hydrate, or solvate thereof, equivalent to 0.2 mg of Compound 1;

a set of solid dosage forms comprising an amount of Compound 1, or a pharmaceutically acceptable salt, hydrate, or solvate thereof, equivalent to 0.3 mg of Compound 1; and a set of solid dosage forms comprising an amount of Compound 1, or a pharmaceutically acceptable salt, hydrate, or solvate thereof, equivalent to 0.6 mg of Compound 1.

13. The kit of claim 2, wherein the plurality of sets of solid dosage forms comprise an initial set of solid dosage forms comprising an amount of Compound 1, or a pharmaceutically acceptable salt, hydrate, or solvate thereof, equivalent to 0.05 mg of Compound 1 once daily in each receiver.

14. The kit of claim 13, wherein the plurality of sets of solid dosage forms comprise a second set of solid dosage forms comprising an amount of Compound 1, or a pharmaceutically acceptable salt, hydrate, or solvate thereof, equivalent to 0.1 mg of Compound 1 once daily in each receiver.

15. The titration package of claim 13, wherein the amount of Compound 1, or a pharmaceutically acceptable salt, hydrate, or solvate thereof, increases by an amount equivalent to 0.05 mg of Compound 1 in each successive row.

16. The kit of claim 2, wherein the plurality of sets of solid dosage forms comprise an initial set of solid dosage forms comprising 0.05 mg of Compound 1 once daily in each receiver.

17. The kit of claim 16, wherein the plurality of sets of solid dosage forms comprise a second set of solid dosage forms comprising 0.1 mg of Compound 1 once daily in each receiver.

18. The kit of claim 16, wherein the amount of Compound 1 increases by 0.05 mg of Compound 1 in each successive row.

19. The kit of claim 2, wherein the initial set of solid dosage forms are configured to be administered for about a week, and each time period is about one week.

20. The kit of claim 2, wherein the pulmonary arterial hypertension (PAH) is selected from:
  idiopathic PAH;
  familial PAH;
  PAH associated with a collagen vascular disease selected from: scleroderma, CREST syndrome, systemic lupus erythematosus (SLE), rheumatoid arthritis, Takayasu's arteritis, polymyositis, and dermatomyositis;
  PAH associated with a congenital heart disease selected from: atrial septic defect (ASD), ventricular septic defect (VSD) and patent ductus arteriosus in a patient;
  PAH associated with portal hypertension;
  PAH associated with HIV infection;
  PAH associated with ingestion of a drug or toxin;
  PAH associated with hereditary hemorrhagic telangiectasia;
  PAH associated with splenectomy;
  PAH associated with significant venous or capillary involvement;
  PAH associated with pulmonary veno-occlusive disease (PVOD); and
  PAH associated with pulmonary capillary hemangiomatosis (PCH) in a patient.

21. The kit of claim 2, wherein the pulmonary arterial hypertension (PAH) is selected from:
  idiopathic PAH;
  familial PAH;
  PAH associated with a collagen vascular disease selected from: scleroderma, CREST syndrome, systemic lupus erythematosus (SLE), rheumatoid arthritis, Takayasu's arteritis, polymyositis, and dermatomyositis; and
  PAH associated with a congenital heart disease selected from: atrial septic defect (ASD), ventricular septic defect (VSD) and patent ductus arteriosus in a patient.

22. The kit of claim 2, wherein the pulmonary arterial hypertension (PAH) is selected from idiopathic PAH and familial PAH.

* * * * *